United States Patent
Vitello et al.

(10) Patent No.: US 9,199,749 B1
(45) Date of Patent: Dec. 1, 2015

(54) ASSEMBLY AND SYSTEM FOR CONNECTING A CLOSURE TO A SYRINGE

(75) Inventors: Jonathan J. Vitello, Fort Lauderdale, FL (US); Patrick Vitello, Fort Lauderdale, FL (US); Omesh Ganesh, Pompano Beach, FL (US)

(73) Assignee: Medical Device Engineering, LLC., Pompano Beach, FL (US)

( * ) Notice: Subject to any disclaimer, the term of this patent is extended or adjusted under 35 U.S.C. 154(b) by 749 days.

(21) Appl. No.: 13/457,314

(22) Filed: Apr. 26, 2012

Related U.S. Application Data

(60) Provisional application No. 61/566,444, filed on Dec. 2, 2011, provisional application No. 61/479,198, filed on Apr. 26, 2011.

(51) Int. Cl.
*A61M 5/00* (2006.01)
*B65B 7/28* (2006.01)
*A61M 5/31* (2006.01)

(52) U.S. Cl.
CPC .............. *B65B 7/2835* (2013.01); *A61M 5/008* (2013.01); *A61M 5/002* (2013.01); *A61M 2005/3104* (2013.01); *B67B 2201/00* (2013.01)

(58) Field of Classification Search
CPC ......... B65B 3/02; B65B 7/2835; A61M 5/00; B67B 2201/00
USPC ........... 53/331.5, 281, 471, 167; 604/11, 192, 604/263; 81/3.33
See application file for complete search history.

(56) References Cited

U.S. PATENT DOCUMENTS

| | | | |
|---|---|---|---|
| 2,834,346 A | 5/1958 | Adams |
| 3,245,567 A | 4/1966 | Knight |
| 3,747,751 A | 7/1973 | Miller et al. |
| 4,216,872 A | 8/1980 | Bean |
| 4,313,539 A | 2/1982 | Raines |
| 4,420,085 A | 12/1983 | Wilson et al. |
| 4,457,445 A | 7/1984 | Hanks et al. |
| 4,530,697 A | 7/1985 | Kuhlemann et al. |
| 4,571,242 A | 2/1986 | Klein et al. |
| 4,667,837 A | 5/1987 | Vitello et al. |
| 4,726,483 A | 2/1988 | Drozd |
| 4,832,695 A | 5/1989 | Rosenberg et al. |
| 4,844,906 A | 7/1989 | Hermelin et al. |
| 5,009,323 A | 4/1991 | Montgomery et al. |
| 5,135,496 A | 8/1992 | Vetter et al. |
| 5,165,560 A | 11/1992 | Ennis, III et al. |
| 5,328,474 A | 7/1994 | Raines |
| 5,458,580 A | 10/1995 | Hajishoreh |
| 5,540,666 A | 7/1996 | Barta et al. |
| 5,558,648 A | 9/1996 | Shields |
| 5,624,402 A | 4/1997 | Imbert |

(Continued)

*Primary Examiner* — Xavier A Madison
(74) *Attorney, Agent, or Firm* — Malloy & Malloy, P.L.

(57) ABSTRACT

An assembly for closing the discharge nozzle of a syringe which is pre-filled with a drug or medication. A syringe in combination with a connecting structure removably maintain and support the closure in an operative orientation, which facilitates the rotational attachment of the syringe and the closure when the closure is in mating engagement with the connecting structure. A subsequent removal of the syringe and connected closure from the container or other type of connecting structure is thereby facilitated. The need for an individual to directly handle or touch the closure during its attachment to the syringe is restricted or eliminated. The closure assembly preferably also includes a tamper evident structure which reduces the chances of tampering with the syringe in order to access its contents.

23 Claims, 16 Drawing Sheets

(56) References Cited

U.S. PATENT DOCUMENTS

| | | | |
|---|---|---|---|
| 5,785,691 A | 7/1998 | Vetter et al. | |
| 5,807,343 A | 9/1998 | Tucker et al. | |
| 5,883,806 A | 3/1999 | Meador et al. | |
| 5,884,457 A * | 3/1999 | Ortiz et al. | 53/468 |
| 5,989,227 A | 11/1999 | Vetter et al. | |
| 6,000,548 A | 12/1999 | Tsals | |
| 6,027,482 A | 2/2000 | Imbert | |
| 6,068,614 A | 5/2000 | Kimber et al. | |
| 6,126,640 A | 10/2000 | Tucker et al. | |
| 6,190,364 B1 | 2/2001 | Imbert | |
| 6,193,688 B1 | 2/2001 | Balestracci et al. | |
| 6,196,998 B1 | 3/2001 | Jansen et al. | |
| 6,280,418 B1 | 8/2001 | Reinhard et al. | |
| 6,394,983 B1 | 5/2002 | Mayoral et al. | |
| 6,485,460 B2 | 11/2002 | Eakins et al. | |
| 6,520,935 B1 | 2/2003 | Jansen et al. | |
| 6,565,529 B1 | 5/2003 | Kimber et al. | |
| 6,581,792 B1 | 6/2003 | Limanjaya | |
| 6,585,691 B1 | 7/2003 | Vitello | |
| 6,726,652 B2 | 4/2004 | Eakins et al. | |
| 6,821,268 B2 | 11/2004 | Balestracci | |
| 6,921,383 B2 | 7/2005 | Vitello | |
| 6,942,643 B2 | 9/2005 | Eakins et al. | |
| 7,141,286 B1 | 11/2006 | Kessler et al. | |
| 7,374,555 B2 | 5/2008 | Heinz et al. | |
| 7,425,208 B1 | 9/2008 | Vitello | |
| 7,437,972 B2 * | 10/2008 | Yeager | 81/3.33 |
| 7,588,563 B2 | 9/2009 | Guala | |
| 7,632,244 B2 | 12/2009 | Buehler et al. | |
| 7,641,636 B2 | 1/2010 | Moesli et al. | |
| 7,735,664 B2 | 6/2010 | Peters et al. | |
| 7,762,988 B1 | 7/2010 | Vitello | |
| 7,918,830 B2 | 4/2011 | Langan et al. | |
| 8,091,727 B2 | 1/2012 | Domkowski | |
| 8,348,895 B1 | 1/2013 | Vitello | |
| 8,353,869 B2 | 1/2013 | Ranalletta et al. | |
| 8,591,462 B1 | 11/2013 | Vitello | |
| 8,597,271 B2 | 12/2013 | Langan et al. | |
| 8,616,413 B2 | 12/2013 | Koyama | |
| 8,864,021 B1 | 10/2014 | Vitello | |
| 8,864,707 B1 | 10/2014 | Vitello | |
| 8,864,708 B1 | 10/2014 | Vitello | |
| 2002/0133119 A1 | 9/2002 | Eakins et al. | |
| 2003/0183547 A1 * | 10/2003 | Heyman | 206/439 |
| 2004/0064095 A1 | 4/2004 | Vitello | |
| 2004/0116858 A1 | 6/2004 | Heinz et al. | |
| 2004/0225258 A1 | 11/2004 | Balestracci | |
| 2010/0084403 A1 | 4/2010 | Popish et al. | |
| 2012/0064515 A2 | 3/2012 | Knapp et al. | |
| 2012/0110950 A1 * | 5/2012 | Schraudolph | 53/331.5 |

* cited by examiner

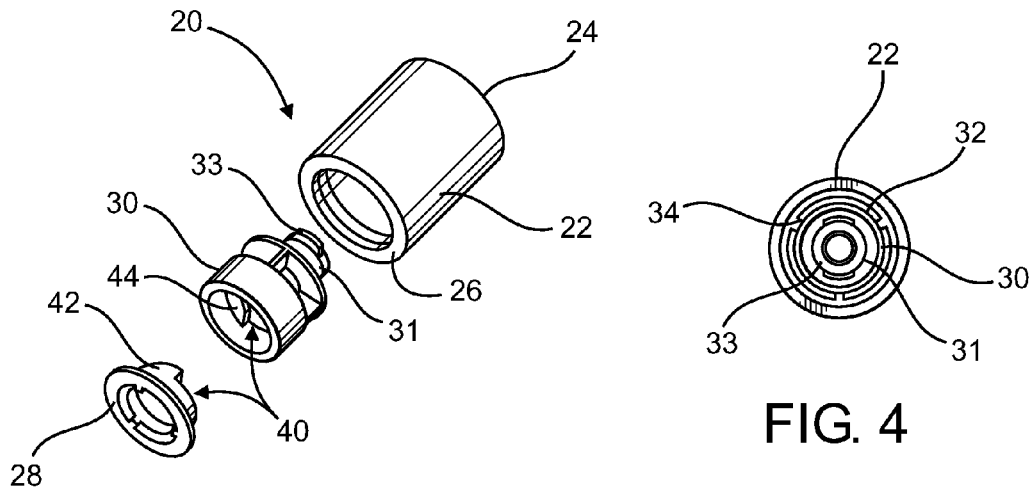
FIG. 3
FIG. 4
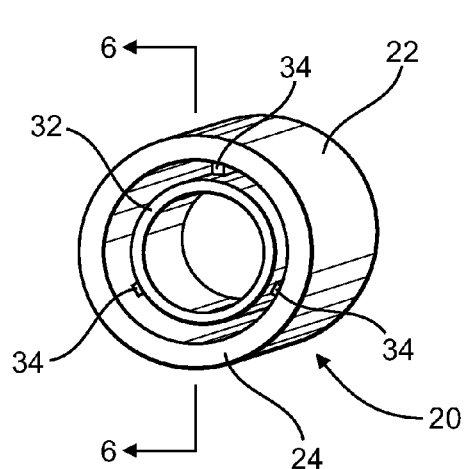
FIG. 5
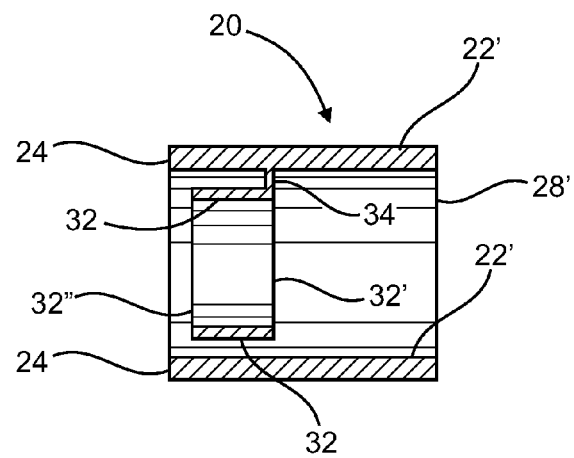
FIG. 6

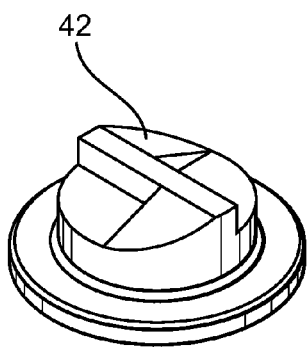
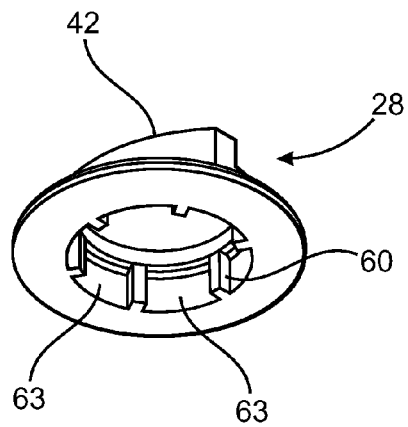
FIG. 7    FIG. 8
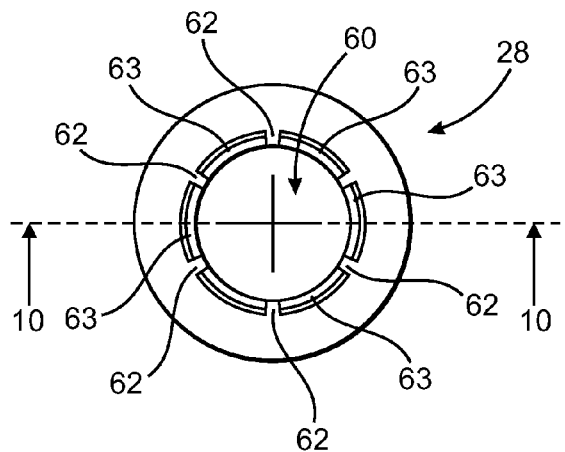
FIG. 9
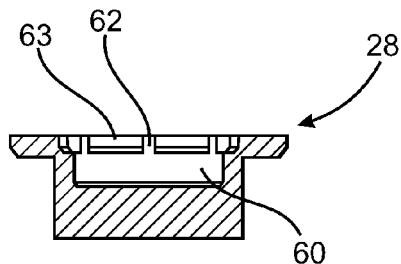
FIG. 10

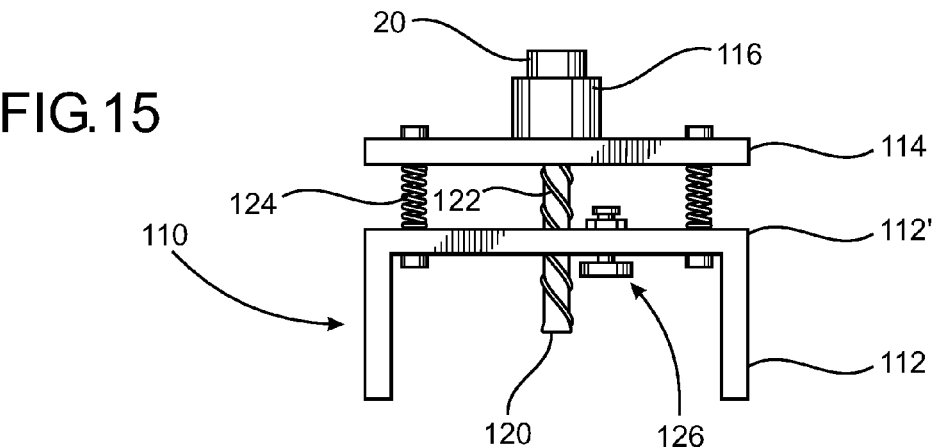
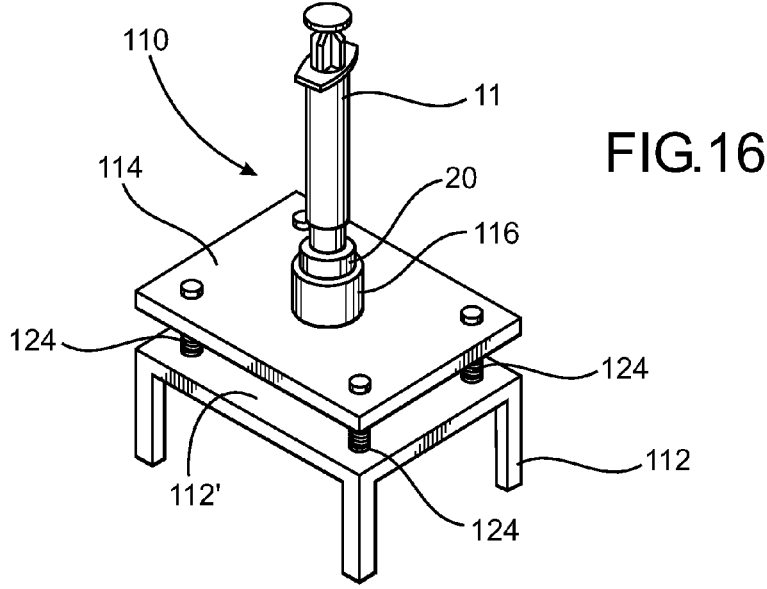
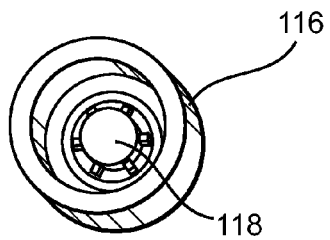

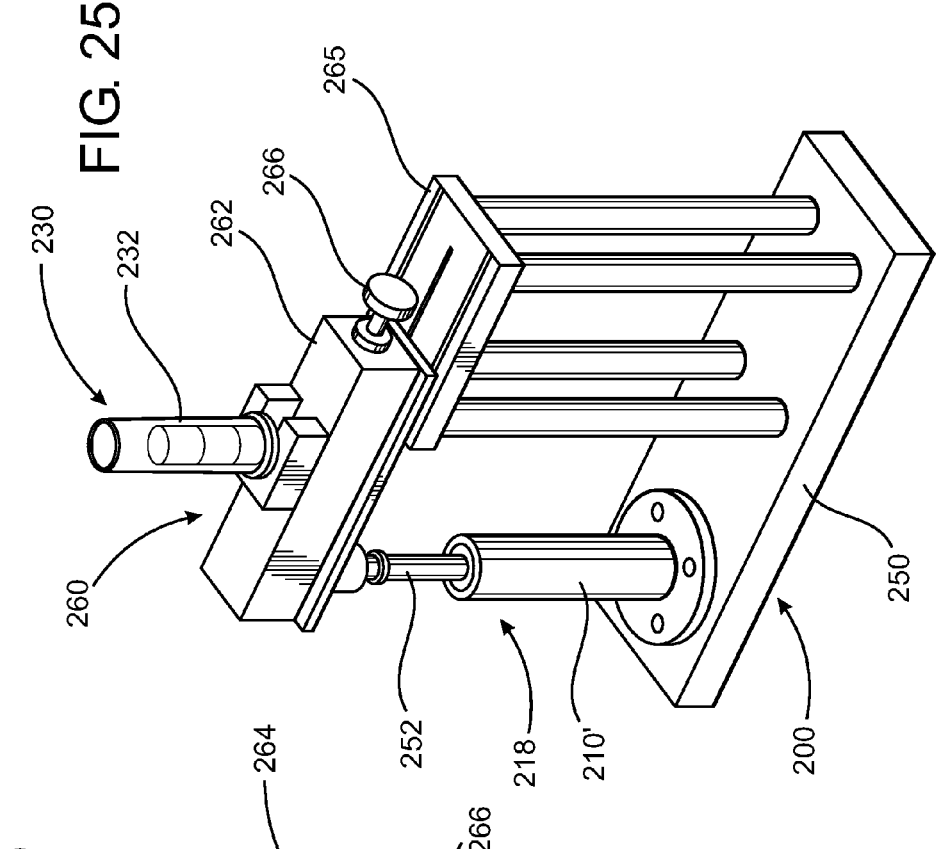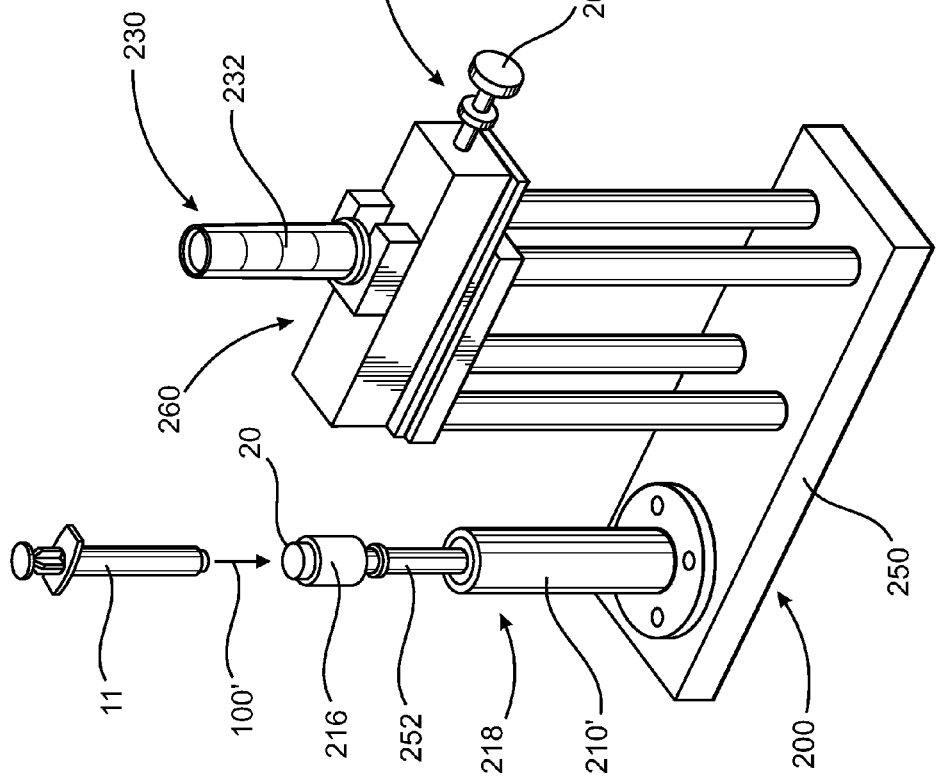

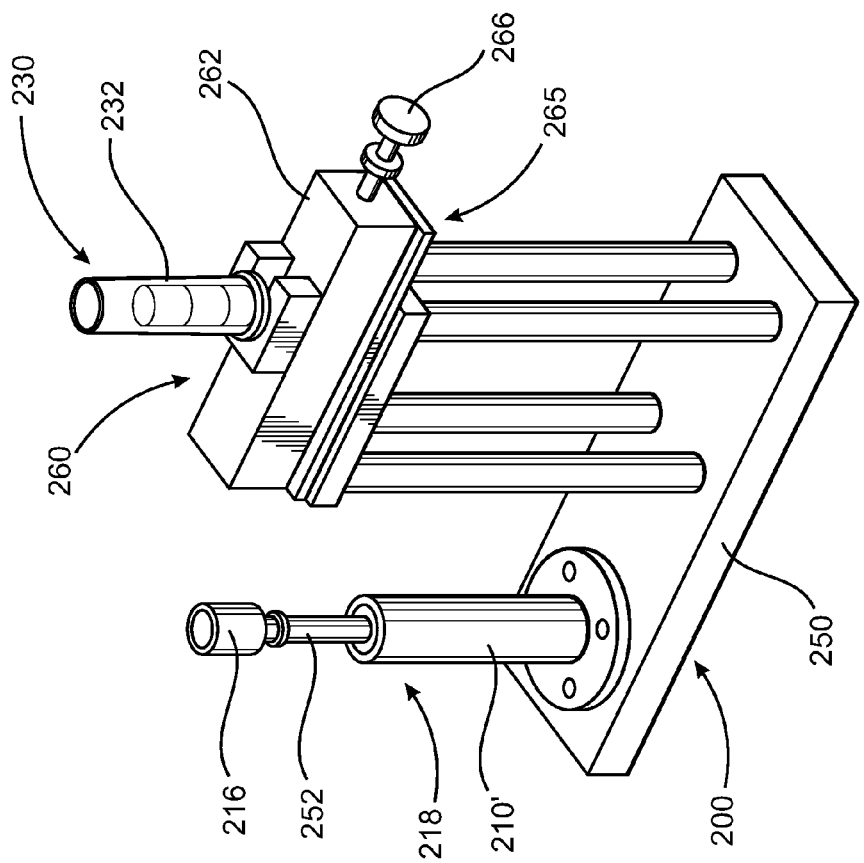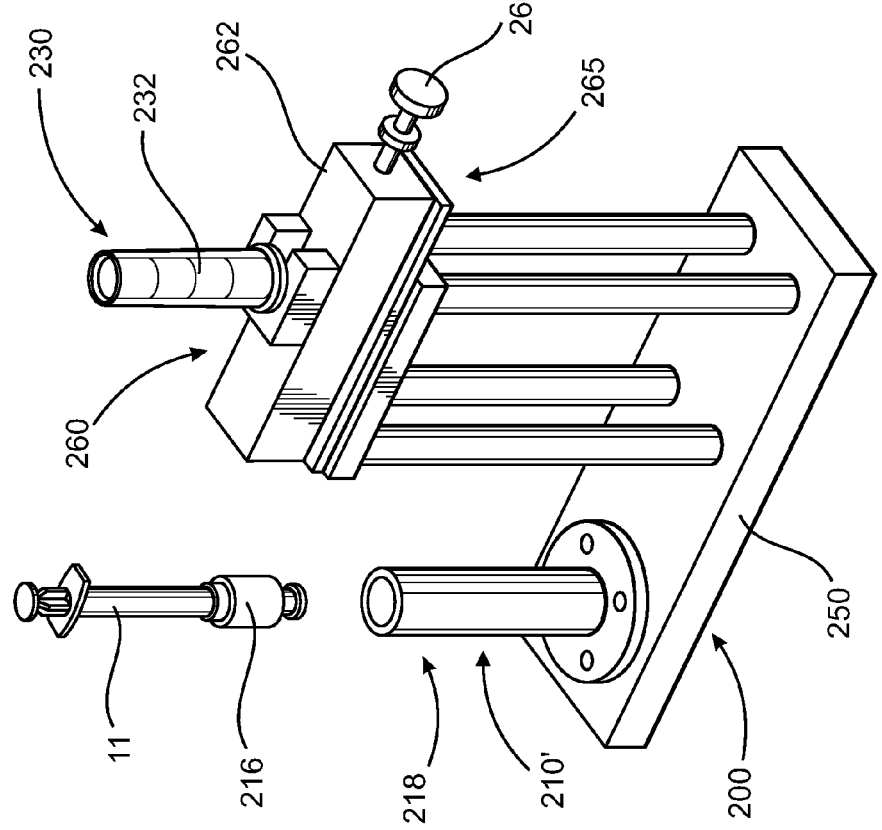

ASSEMBLY AND SYSTEM FOR CONNECTING A CLOSURE TO A SYRINGE

The present Non-Provisional patent application claims priority pursuant to 35 U.S.C. Section 119(e) to a currently and prior filed Provisional patent application, namely, that having Ser. No. 61/566,444 filed on Dec. 2, 2011, as well as to another currently and prior filed Provisional application, namely, that having Ser. No. 61/479,198 filed on Apr. 26, 2011, the contents of which are incorporated herein by reference in their entireties.

BACKGROUND OF THE INVENTION

1. Field of the Invention

The present invention is directed to an assembly for closing the discharge port of a syringe, after the syringe has been filled with a medicine to be administered to a patient, with a closure thereof structured to eliminate or at least significantly reduce the need for an individual to directly handle or touch the closure during its attachment to the syringe. The closure assembly of the present invention may also include a tamper evident structure to eliminate or significantly reduce the chances that someone will tamper with the syringe filled with medicine. The present invention is also directed to a connecting structure, which may or may not be directly associated with a container, and which includes at least one connector cooperatively structured with the closure to removably maintain and support the closure in an operative orientation. The operative orientation facilitates the rotational attachment of the syringe to the closure when the closure is in mating engagement with the connecting structure.

2. Description of the Related Art

It is very common for medical doctors and other authorized medical personnel to order that a patient be given a drug or medication by injection. In fact, it is currently estimated that more than 16 billion injections are administered on a worldwide basis in any given year. Clearly, a number of safety issues are associated with giving injections. One top concern relates to the avoidance of contamination by bacteria, germs or other microbial organisms.

As a result, it is becoming relatively common in hospital settings for a number of syringes to be pre-loaded or filled by a pharmacist, or other authorized personnel within a hospital or similar facility, at an appropriate location for subsequent dispensing of same to one or more patients. The pharmacy or other location where syringes are filled can and often will be located in a remote part of the hospital, relative to the patient care area where the injection is to be administered. In some cases, the loading of syringes occurs in another building or facility entirely, often referred to as "third party pharmacies." This may even be a growing trend among hospitals to limit certain costs. Regardless, a syringe filling station at a large medical facility may resemble a factory, from which drug loaded syringes are delivered to a large number of nurse's stations in multiple hospital or medical buildings. Because many nurse's stations are typically located very remote and from a syringe filling station, a loaded syringe is quite often given to another person for delivery to a nurse's station, for subsequent dosing of the patient by qualified personnel.

From the foregoing, it may be understood that during the course of loading a syringe with a drug, and also afterwards, when a loaded syringe is delivered to a nurse's station, or even subsequently to a patient, the syringe can easily be handled by more than just one or two people. This, in turn, increases the chance for the syringe to become contaminated, by exposure to bacteria, germs, etc., which could possibly then be introduced into a patient's body tissues, and which could potentially lead to infection, presenting in turn, dangerous and possibly fatal effects on the patient. Consequently, and from the above, the concern for and the high level of importance associated with maintaining the sterility of a syringe will be better understood.

Also, and especially in the case of a very expensive drug or an addictive drug, such as but not limited to morphine, there is some danger that a pre-loaded syringe will be tampered with by a person seeking to improperly gain access to the drug, whether to use it himself, or to try to sell it illegally. A resulting danger also exists in that if an unauthorized person were actually to access to the prescribed medicine, he or she might inappropriately substitute saline solution or some other unauthorized substance in the syringe in an effort to avoid detection. By way of example only, if saline solution were substituted for a dose of morphine, this could have extremely serious consequences. Thus, the growing use of syringes which are pre-loaded with a drug presents another problem in that it is important to know if the sealed and/or pre-loaded syringe has, or has not, been tampered with and exposed to contamination or might otherwise have been compromised.

The benefits of using a pre-filled syringe, and of being able to readily determine whether or not it has been tampered with, are abundantly clear. Drugs and medications are specific to each particular patient's disorder or disease being treated. In addition, interactions between drugs and medications given to a patient incorrectly can have serious and deadly consequences. It is, therefore, important to know that a particular medication being injected is, in fact, the drug that was prescribed by the treating physician, and that it has not been replaced by another compound. Moreover, some drugs can have harmful effects in large doses. Accordingly, it is also important to ensure that the proper dosage is followed, as prescribed. Since pre-filled syringes are prepared in advance of being delivered and used, they may be loaded carefully by a pharmacist or other similarly qualified individual to ensure the appropriate medication and dose is prepared. This reduces errors on injection by nurses or physicians who may be in a stressful or time-sensitive situation and may not have the luxury of verifying the correct medication or measuring out a dose, particularly small doses, from a source vial.

Pre-filled syringes are also particularly useful in view of the recent shortage of medications and other injectables, such as narcotics or epinephrine for example. Some drugs and medications, even those which are essential for treating life-threatening diseases, are currently in drastically short supply, due to several factors. For example, during the manufacturing process of some medications, it can occur and has happened for whole batches to become contaminated, such as by bacteria or other microorganisms that could cause infection upon injection, thereby rendering quantities of medications unusable, which in turn, reduces the overall stock of available medications. In addition, manufacturing capacity issues, such the availability and increased cost of raw materials and transportation, as well as lower profit margins, are contributing factors that also result in reduced quantities of medications being produced, and therefore, available to patients. Accordingly, the supply of drugs that are available and safe for use is a starting to be viewed as a precious commodity, with little to no room for waste. The use of pre-filled syringes helps significantly to ensure that only the exact amount of medicine or drugs prescribed are being used, thereby helping to eliminate waste. Also, by having a pharmacist or other qualified person at a filling station preparing the pre-filled syringes, even at a location distant from the patient treatment site helps to ensure that the exact amount of medication needed is delivered. This also circumvents the theft of drugs by "accidental" taking of excess medication, such as to siphon some off for personal use or another non-prescribed purpose, which has unfortunately been known to occur. Accordingly, the use of pre-filled syringes helps maintain the stock of these important drugs so that they may be available to the patients truly in need of them. Further, any unused pre-filled syringes may be recycled so that unused medication does not go to waste. This is only possible, however, if there is some way to determine that a pre-filled syringe has not been tampered with or compromised, thereby verifying the integrity of the contents.

Despite attempts in the past to prevent unauthorized access to syringe(s) pre-loaded with a drug or medication, it is understood that some problems continue to exist in this field of art. Such problems include the ability to manufacture syringes, and/or accessories therefor, in an inexpensive and yet effective manner. Other problems exist relative to the number of people that might handle pre-filled syringes, which in turn, poses a challenge to maintaining the sterility of the syringes and/or accessories, whether during storage at the manufacturing facility, during the transport thereof from such a facility to a hospital or other medical facility, and then to a nursing station and ultimately, to a patient care area.

Accordingly, there is a need in the relevant field of art for an improved syringe closure that is capable of being used with standard or conventional pre-loaded syringes. If any such improved syringe closure were developed, it would be structured in a manner which overcomes problems and or disadvantages of the type set forth above or otherwise known to still exist in this field of art. In addition, the use and application of any such improved syringe closure, were one developed, would preferably be facilitated by the provision of a closure support, which may be in the form of a container or tray. Ideally, if any such combination of a closure and a support therefor were developed, it would have certain structural and operative features which would facilitate appropriate connection of the closure to a conventional pre-loaded syringe in an efficient manner which would eliminate or at least significantly reduce the need for an individual to directly handle or touch the closure during its attachment to the syringe. In addition, any such improved closure, if developed, would preferably also be structured to provide a clear and unmistakable indication of tampering or of previous attempted access to the contents of the preloaded syringe. Finally, if any such improved closure and support for the closure were developed, it would also preferably be structurally and operatively reliable, while still remaining relatively easy and cost effective to make and use, in order to facilitate widespread use and acceptance throughout the medical profession.

SUMMARY OF THE INVENTION

The present invention is intended to present a solution to these and other needs which remain in the relevant field of art, and as such, is directed to a closure assembly structured for being protectively connected to a syringe of the type including a nozzle and a discharge port. As will be described in greater detail subsequently herein, the inventive assembly includes a closure and a connecting structure for the closure. The closure assembly may further include a tamper evident assembly to provide a clear indication of attempted or accomplished access to a drug or medication contained within a pre-loaded syringe.

In at least one preferred embodiment, the present invention comprises a closure, which may include an end cap member and a syringe cap, with the latter being structured for rotational attachment to a syringe. When the inventive closure assembly is rotationally attached to a syringe, the syringe cap is disposed to close, restrict and/or prevent fluid flow from the discharge port of the syringe nozzle. Moreover, the closure may be structured to include a tamper evident assembly within the end cap member to provide a clear indication of attempted or accomplished access to the contents of the pre-loaded syringe.

In addition, the end cap member includes an open end and a substantially oppositely disposed closed end, wherein the open end is dimensioned to receive the discharge port and/or nozzle of the syringe there through into the interior thereof to accomplish the aforementioned rotational attachment. The closed end of the end cap member is fixedly secured, such as by sonic welding, to the end cap member so as to move therewith and at least partially segregate an interior portion of the end cap member from an exterior of the closed end. The syringe cap is disposed within the interior of the end cap member and is structured for the rotational attachment to the syringe in a manner which serves to close or cover the nozzle in substantially flow restricting position relative to the discharge port of the syringe. Therefore, as should be apparent, the rotational attachment between the syringe cap of the end cap member and the syringe is accomplished by relative rotation between the syringe and the closure and more specifically, the syringe and the syringe cap.

In certain instances, the syringe cap may be at least partially movable within the interior of the end cap member. Accordingly, a drive assembly is disposed on the interior of the end cap member and is structured to facilitate the rotational attachment of the syringe cap to the syringe. As described in greater detail hereinafter, the drive assembly is formed on interior portions of both the syringe cap and a correspondingly disposed interior portion of the closed end of the end cap member. Structuring of the drive assembly is such that the syringe cap will be prevented from rotating within the interior of the end cap upon a confronting interaction between different portions of the drive assembly which, as set forth above, are located on interior portions of the syringe cap and the closed end portion of the end cap member. As a result of the interaction of the different portions of the drive assembly, the syringe can be at least partially inserted into the open end of the end cap member, such that rotation of the syringe relative to the syringe cap is facilitated by the syringe cap being disposed in a fixed orientation on the interior of the end cap member. A continued and sufficient rotation of the syringe relative to the syringe cap will accomplish the aforementioned rotational attachment there between and an effective mounting or securing of the closure to the syringe in closing, covering and/or flow restricting relation to the nozzle and/or discharge port of the syringe.

Another operative and structural feature of one or more preferred embodiments in the present invention is the provision of a connecting structure including at least one connector. The connecting structure, including the at least one connector, may be a part of, formed on and/or attached to a support base, wherein the support base is integrated into a container. As such, the support base may comprise a floor portion or other inner portion of the container. Moreover, the connecting structure and the container are ideally structured to contain one or more of the closures on the interior thereof, wherein the one or more closures are maintained in an operative orientation. In addition, one connector is, or a plurality of such connectors, are preferably equal or sufficient in number to retain the number of closures intended to be disposed within the container. Also, in at least one preferred embodiment, the container associated with the at least one connector is of the type structured to accomplish the "commercial packaging" of the one or more closure, wherein such commercial packaging is intended for storage, transport, and delivery of the closure(s) from a manufacturer or distributer to a point or location of use.

Each of the one or more connectors is structured to be disposed in removable mating engagement with the closed end of a corresponding closure or end cap member. Accordingly, when the closure is in the removable mating engagement it is disposed in an operative orientation, which facilitates receipt of the syringe within the corresponding closure and end cap. In at least one embodiment of the present invention, the operative orientation may be more specifically described as comprising the closed end disposed in the removable mating engagement with the one connector, while said open end is exposed to the syringe in a manner which facilitates the rotational attachment between the syringe and the closure. Accordingly, the operative orientation of the one or more closures and end cap members, when disposed on the connecting structure, facilitates the aligned insertion of a portion of the nozzle of the syringe into the end cap member and the aforementioned rotation of the syringe relative to the syringe cap. As a result, the rotational attachment of the syringe and the syringe cap will be efficiently accomplished. Once attached, the syringe and the connected closure can both be removed from the support base and container, without any unnecessary handling of the closure.

More specifically, each of the one or more connectors is cooperatively structured with the closed end of each of the end cap member to define a "rotationally restrictive" connection between the end cap member or closure and the connecting structure. Such a rotationally restrictive connection there between will be sufficient to prevent or at least substantially restrict rotation of the end cap member in either of two opposite directions, relative to the connecting structure and corresponding container, while the nozzle of the syringe is being inserted into the interior of the end cap member and rotated relative to the closure, syringe cap and end cap member. In more specific terms, the rotationally restrictive connection comprises the closure being disposed in substantially rotationally fixed position relative to the one connector and the support base, concurrently to a rotation of the syringe relative to the closure, thereby facilitating the rotational attachment of the syringe to closure. For purposes of clarity, the term "substantially rotationally fixed" is intended to describe, but not be limited to, the closure being restricted from rotating relative to the one connector, to the extent that at least a minimal amount of rotational sliding or "slippage" type movement may occur there between. This would be due to the configurations and/or dimensions of confronting portions and/or surfaces of the one connector and the closed end of the one closure, when disposed in the removable mating engagement with one another.

The aforementioned rotational attachment of the syringe and the syringe cap is further facilitated by a threaded engagement of the syringe and the syringe cap, along correspondingly and cooperatively structured portions thereof. Once the rotational attachment has been established, the corresponding, connected closure can be removed from the connecting structure and one connector and/or from the interior of the container, by a lifting or other outwardly directed force being applied to syringe.

The present invention includes additional preferred embodiments directed to an at least partial "automatic" securing of a closure to a syringe primarily of the type intended for use with a syringe, pre-loaded with medicine. As used herein, the term "automatic" refers to the ability to attach the closure to the syringe in a manner which does not normally require the handling or touching of the closure(s). Also, some of these additional embodiments are directed to the substantially "automatic" securing of a closure to a syringe, wherein the closure itself may comprise a structure equivalent to that which has already been described herein or which will be described later herein relative to other preferred embodiments of the present invention. More specifically, each of a plurality of closures will preferably include a closure having a fixed closed end and which is structured for rotational attachment to the syringe. Further at least some of the embodiments of the present invention may be directed to closures which include an end cap that has a fixed closed end and a syringe cap disposed on an interior thereof. The syringe cap is structured for rotational attachment to a corresponding portion of the syringe in a manner which serves to close or cover the discharge port of the syringe, as more fully described herein.

Structural and operative features which render at least some of the preferred embodiments substantially "automatic" include a connecting structure having at least one connector rotationally mounted on a platform or a remainder of a connecting structure. In addition, the at least one connector is disposable into removable mating engagement with the closed end of the closure, which is to be attached to the syringe. Moreover, the one connector and the closed end of the closure are cooperatively structured to define the aforementioned "rotationally restrictive" connection there-between, as well as an operative orientation of the closure, when the one connector is in the removable mating engagement therewith.

The rotationally restrictive connection between the one connector and the closed end of the closure is at least partially defined by the aforementioned, substantially rotationally fixed positioning of the closure and closed end on the one connector, while in the operative orientation. A concurrent rotation of the closure with the one connector is thereby accomplished, as the one connector rotates relative to the remainder of the connecting structure. It is also emphasized that the operative orientation of the closure, when connected to the one connector serves to position the closure in a substantially upright position or other position which facilitates the receiving of the discharge port of the syringe therein. Further, the operative position of the closure and its ability to concurrently rotate with the one connector facilitates the aforementioned rotational attachment of the syringe to the closure such as with, but not limited to, the syringe cap portion of the closure.

Yet another embodiment of the present invention is also directed to an assembly for the "automatic" securing of at least one closure to a discharge port of a syringe and also includes a connecting structure. In addition, the connecting structure includes at least one connector rotationally mounted thereon and disposable in removable mating engagement with a predetermined portion of the closure to be secured to the syringe. As also set forth above, the removable mating engagement between the connector is accomplished by the one connector being correspondingly configured and cooperatively structured with the closed end comprising a predetermined portion of the closure. As such, the aforementioned rotationally restrictive connection between the one connector and the closed end of the closure is defined. Such rotationally restrictive connection facilitates a substantially fixed disposition of the closure on the connector in an operative orientation and also, allows a concurrent rotation of the closure with the one connector, preferably relative to the syringe, to which the closure is rotationally attached.

Distinguishing structural and operative features of this additional embodiment of the automatic securing assembly includes a delivery assembly comprising a carriage assembly. The carriage assembly is disposed adjacent to the connecting structure and in communicating relation therewith. More specifically, the carriage assembly is structured to support at least one closure and be movable with the closure into and out of a "delivering" position relative to the one connector. Moreover, a positioning assembly comprising at least one positioning member is disposable in "positioning engagement" with the one closure and structured for the positioning of the closure into a "delivering orientation" relative to the one connector. As such, the positioning member may take the form of a plunger or other appropriate structure accessible from an exterior of the carriage. When manipulated, either manually or mechanically, the plunger will move the carriage into the aforementioned delivering position and concurrently engage and move the at least one closure into the delivering orientation. In addition, the carriage is structured to include a release portion disposable in direct communicating relation and/or aligned orientation with the connector when the connector is in the receiving position, as described above.

It is further noted that in additional embodiments of the automatic assembly, the carriage may be directly associated with a closure supply that is preferably, but not exclusively, defined by a canister. When utilized, the canister is dimensioned and configured to store a plurality of the closures on the interior thereof, in a generally aligned relation to one another. An operative connection of the canister or closure supply relative to the carriage will facilitate a gravitational feed of each of the closures contained therein, successively onto the carriage. In cooperation therewith, the positioning member will engage each of the closures successively as they exit the canister. The continued manipulation of the positioning member or plunger will serve to successively "index" or dispose an outer or end most one of a plurality of closures supported on the carriage, into the delivering orientation. Accordingly, the positioning member is further structured to reciprocally and/or successively dispose the carriage between the aforementioned delivering position and a "supplied" position. When in the supplied position, appropriate portions of the carriage are disposed in direct communication with the closures as they successively exit the canister or closure supply. Further manipulation of the connector member will serve to facilitate the exiting of the next closure from the open end of the canister onto the carriage, which is facilitated by the above noted gravitational feed.

It is further emphasized that in each of the preferred embodiments of the present invention, the at least one connector of the connecting structure is cooperatively configured with a predetermined portion of the closure, and most preferably, a closed end of the closure, so as to define the aforementioned rotationally restrictive connection. Moreover, in at least one embodiment the cooperative and corresponding configuration of the connector with the closed end of the closure is defined by the connector and the closed end including a plurality of projections extending outwardly from corresponding surfaces of the connector and closed end and disposed in equally spaced relation to one another. Further, the plurality of projections on both the connector and the closed end may be, but are not limited to, being collectively disposed in a circular or annular array. Such corresponding configurations of the one connector and the closed end, thereby facilitates being automatically disposed in the removable mating engagement with one another, without requiring any additional adjustment or manipulation of the closure to accomplish the mating engagement and rotationally restrictive connection.

Yet another preferred embodiment of the present invention is directed to a substantially "automatic" system or assembly for securing each of a plurality of closures to different ones of a plurality of syringes. Structural and operative features of this additional embodiment include a connecting structure comprising at least one connector rotationally mounted thereon and disposable in removable, mating engagement with the closed end of each of the plurality of closures. Further, the at least one rotationally mounted connector is cooperatively structured with a predetermined portion, such as the closed end of each of the closures, to define the aforementioned rotationally restrictive connection there between and the concurrent maintenance of each of the plurality of closures in the aforementioned operative orientation.

Additionally, a delivery assembly includes a closure supply comprising a canister or like container in which the plurality of closures to be attached are stored. The delivery assembly also includes a positioning assembly operatively disposed between the canister of the supply assembly and the connecting structure. Operative features of the positioning assembly serve to dispose individual ones of the plurality of closures from the canister of the closure supply into a delivering orientation which may be equivalent to the operative orientation on the connector rotationally mounted on the connecting structure.

More specifically, the canister and the positioning assembly are cooperatively disposed and structured to facilitate a gravitational passage or feeding of the plurality of closures from within the canister into an operative relation to the positioning assembly. The positioning assembly comprises at least one positioning member disposed and structured to perform a "positioning engagement" with each of the plurality of closures individually, upon their exiting from the canister. Successive positioning engagement with each of the closures accomplishes what generally may be referred to as an "indexing" of successive ones of the closures into the operative orientation and rotationally restrictive mating engagement with the at least one connector of the connecting structure.

The present invention is also directed to a closure supply that includes a container and a plurality of closures randomly and removably disposed therein. Such container has no connecting structure, so the closures are free to move and/or rotate within the container, and are in no particular fixed position. Moreover, the container of the closure supply includes at least one section made of a gas-permeable material to facilitate the sterilization of closures retained therein.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 3 is an exploded perspective view of the closure of the embodiment of FIG. 1.

FIG. 4 is an end view of the closure, as viewed from the open end of the closure, illustrated in the embodiment of FIG. 3.

FIG. 5 is an interior perspective view of an end cap member of the closure represented in FIGS. 1, 3 and 4.

FIG. 6 is a transverse sectional view along line 6-6 of FIG. 5.

FIG. 7 is a perspective view in detail of the closed end of the end cap member in the embodiment of the closure illustrated FIGS. 1 and 3.

FIG. 8 is a bottom perspective view of the closed end of the end cap member shown in FIG. 7.

FIG. 9 is an exterior plan view of the closed end of the end cap member shown in FIGS. 7 and 8.

FIG. 10 is a sectional view along line 10-10 of FIG. 9.

FIG. 15 is a side view of the present invention in another preferred embodiment and directed to a substantially automatic attachment of a closure assembly to a syringe.

FIG. 16 is a perspective view of the invention shown in the embodiment of FIG. 15.

FIG. 17 is an interior perspective view of one connector associated with the connecting structure of the invention illustrated in the embodiment of FIGS. 15 and 16.

FIG. 23 is a perspective view of the present invention in an additional preferred embodiment and illustrating one stage of operation of same.

FIG. 24 is a perspective view of the invention in the embodiment shown in FIG. 23 and illustrating a next succeeding step in the operation of same.

FIG. 25 is a perspective view of the embodiments of FIGS. 23 and 24 in a next succeeding step of operation.

FIG. 26 is a perspective view of the embodiments of FIGS. 23 through 25 in a next succeeding step of operation.

Like reference numerals refer to like parts throughout the several views of the drawings.

DETAILED DESCRIPTION OF THE PREFERRED EMBODIMENT(S)

Figure 2:
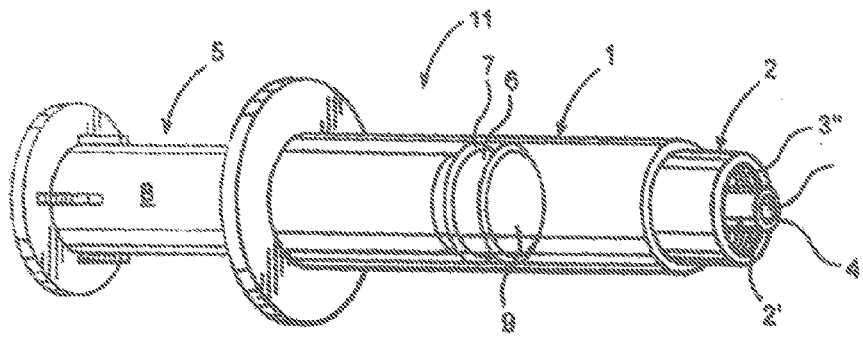
FIG. 2 is a prior art representation of a standard or conventional syringe.

As indicated in the accompanying drawings, the present invention is directed to an assembly for closing a conventional syringe 11, such as that shown in FIG. 2 and labeled as "Prior Art," which in most cases, will be pre-loaded with a drug or medication. The inventive assembly includes a closure, generally indicated as 20, structured for use in combination with a support base 50.

Before describing the structural and operative features of the present invention, it will be helpful to initially refer to a conventional or standard type of syringe 11, such as that shown in FIG. 2, in order to offer some understanding of the environment in which the present invention will operate. As such, and as shown in FIG. 2, the syringe 11 typically includes a barrel 1 and a nozzle structure 2. The barrel 1 comprises an elongate interior chamber disposed in fluid communication with an axial passageway or channel 3 on the interior of the nozzle portion 2'. Also, the nozzle portion 2' may comprise a luer type fitting. The channel 3 is to be considered a portion of the nozzle structure 2 and terminates distally at an opening or discharge port 4. A piston 5 is structured to slide within the barrel 1 and includes a head 6 provided with a circumferential gasket 7. When assembled, the end face 9 of the head 6 of the piston 5 confronts the interior end of the channel 3 and closes the discharge port 4. The piston also includes a push rod or plunger 8 connected to the head 6, which is dimensioned to pass into the barrel 1. In use, the standard type syringe 11, after being loaded with a drug, medicine or other contents, may be closed or sealed by covering the discharge port 4 with the closure assembly 20 of the present invention. Accordingly, the nozzle structure 2 preferably includes an inner connecting surface 3" or other appropriate connecting structure, such as a ribbed or threaded surface. Therefore, and as has been represented, the interior connecting surface or portion 3" and the nozzle portion 2' can be and should be considered a part of the nozzle 2 for purposes of this description.

Before any of the embodiments of the present invention are described, it is to be understood that the invention is not limited in its application to the details of construction and/or the components set forth in the following description or to the illustrations shown in the accompanying drawings. The invention is capable of other embodiments and of being practiced and/or of being carried out in various ways. Also, it is to be understood that the phraseology and terminology used herein is the for the purpose of description and should not be regarding as limiting. The use of the words "including," "comprising" or "having" and variations thereof is meant to encompass the items listed thereafter and equivalents thereto, as well as additional items.

Referring now to FIGS. 1 and 3-6, the structural and operative features of the inventive assembly will be described in at least one embodiment, as illustrated therein. In this embodiment, the closure assembly for a syringe comprises a closure 20 that includes an end cap member 22 having a substantially hollow interior. The end cap member 22 also includes an open end 24 and an oppositely disposed closed end 28. As also represented in FIGS. 7-10, the closed end 28 is integrally connected to and ideally fixedly connected to the end cap member 22 and moves therewith. The closed end 28 is disposed to segregate at least some interior portions of the end cap member 22 from an exterior thereof.

As shown in FIG. 3, the closure 20 also includes the provision of a syringe cap 30 that is structured, dimensioned and configured to be disposed within the interior of the end cap member 22 in interactive relation with the closed end 28. Moreover, the syringe cap 30 is designed to be disposed in closing and/or covering relation to the portion of the nozzle 2' so as to restrict fluid flow from the discharge port 4. The intended closing, covering, and/or flow restricting relation of the syringe cap 30 relative to the nozzle portion 2' is accomplished by the closure 20 and more specifically, the syringe cap 30 being rotationally attached to surface 3" of the nozzle 2 of the syringe 11.

Referring now to FIGS. 5 and 6, the closure 20 may include, in at least one embodiment, the provision of a tamper evident assembly, comprising an indicator member 32. The indicator member 32 preferably includes an annular or ring-shaped configuration. In addition, the indicator member 32 is at least initially connected, but removably connected, to the interior surface portions 22' of the end cap member 22 as best shown in FIG. 6, by at least one, but more practically, a plurality of frangible members 34. The opposite ends of the indicator member 32 are open, as at 32' and 32". Further, the inner, transverse dimension or diameter of the indicator member 32 is sufficient to receive at least a leading portion 31 of the syringe cap 30 there-through, when the closure 20 is fully assembled, with the leading portion 31 being perhaps best shown in FIG. 3.

As also shown in FIG. 3, the leading portion 31 of the syringe cap 30 will have in the preferred embodiments outwardly extending tabs, ears and/or partial thread members 33. These tabs, ears or thread members 33 are disposed, configured and structured to interact with the threaded or ribbed interior surface 3" of the syringe's nozzle structure 2. Accordingly, when the various components of the end cap member 22 are assembled, the syringe cap 30 and in particular, the partial thread members 33 are disposable to interact with the threaded surface 3" to accomplish the intended rotational attachment between the closure 20 and the syringe 11. Such rotational attachment is accomplished by a relative rotation of the syringe 11 and the closure 20 and the syringe cap 30, once the syringe cap 30 is assembled on the interior of the end cap member 22. Such rotational attachment is further defined by a mating interaction of the partial thread members 33 on leading portion 31 and the threaded or ribbed surface 3", once a coaxial alignment and insertion is established between the nozzle portion 2' of the syringe 11 and the end cap member 22 and the syringe cap 30. Such an axial alignment and insertion is at least partially, schematically represented as 100 in FIG. 1 and may be partially defined by the nozzle portion 2' protruding through the open end 24 of the end cap member 22, the open end 32" of the indicator member 32 and into the open end of the leading portion 31 of the syringe cap 30. When properly inserted, the threaded members or tabs 33 will be aligned with the threaded surface 3" of the syringe 11. With specific reference to the one or more embodiments of FIGS. 1-14, when the syringe 11 is aligned, as at 100, with one of the closures 20, it may be rotated relative to the closure 20 and syringe cap 30, as schematically represented as 102 in FIG. 1, to accomplish the intended rotational attachment of the syringe 11 and the closure 20, and more specifically, the syringe nozzle portion 3" to syringe cap 30.

Referring again now to FIG. 3, in order to further facilitate the aforementioned rotational attachment between the closure 20 and the syringe 11 and/or nozzle portion 2', the closure 20 includes, in at least the represented embodiment, a drive assembly 40 comprising cooperatively structured drive portions 42 and 44. For instance, and in the illustrated embodiment, the drive assembly 40 will effectively offer rotation in only one direction, because each of the drive portions 42 and 44 include a "ramp and cliff" structure. This "ramp and cliff" structure of each of the drive portions 42 and 44 provides for a fixed positioning of the syringe cap 30 on the interior of the end cap member 22, when the drive portions 42 and 44 are disposed in abutting or confronting relation with one another, and when the end cap member 22 is rotated in one, predetermined direction. As a result, the attempted rotation of the end cap member 22 in a direction opposite to the one, predetermined direction will result in relative rotation of the end cap member 22 and the syringe cap 30.

Accordingly, the one way drive assembly 40, defined by the aforesaid preferred "ramp and cliff" structure of the drive portions 42 and 44 will mandate that the syringe cap 30 and the end cap member 22 rotate in a common direction, defined by the above-described, one predetermined direction. Therefore, rotational attachment between the outwardly extending tabs, ears and/or threaded members 33 and the interior threaded surface 3" of the syringe and the nozzle structure 2, respectively, is accomplished by a rotation of the end cap member 22 in the aforementioned predetermined one direction relative to the syringe 11, thereby defining the aforementioned rotational attachment between the syringe cap 30 and nozzle structure 2 of the syringe 11.

It may be appreciated from the above description and the appended drawings that the tamper evident assembly, which comprises indicator member 32, allows for the detachment of indicator member 32 from the interior of the end cap member 22' shown in FIG. 6, by a pulling force being exerted on the closure 20 and more probably, on the outer wall of the end cap member 22. This, in turn, causes the frangible members 34 to rupture and be displaced from their interconnecting relation between the indicator member 32 and the interior surface 22' of the end cap member 22. As such, the removal of the end cap member 22, by virtue of a pulling force being exerted thereon, provides a clear indication that access has been attempted to the drug contained within the syringe 11, due to the fact that the syringe cap 30 will still remain in rotational attachment with the nozzle structure 2 and the indicator member 32 will remain in surrounding relation to the syringe cap 30 and/or portions of the syringe, and/or nozzle 2', after a forced removal of the end cap member 22.

Figure 1:
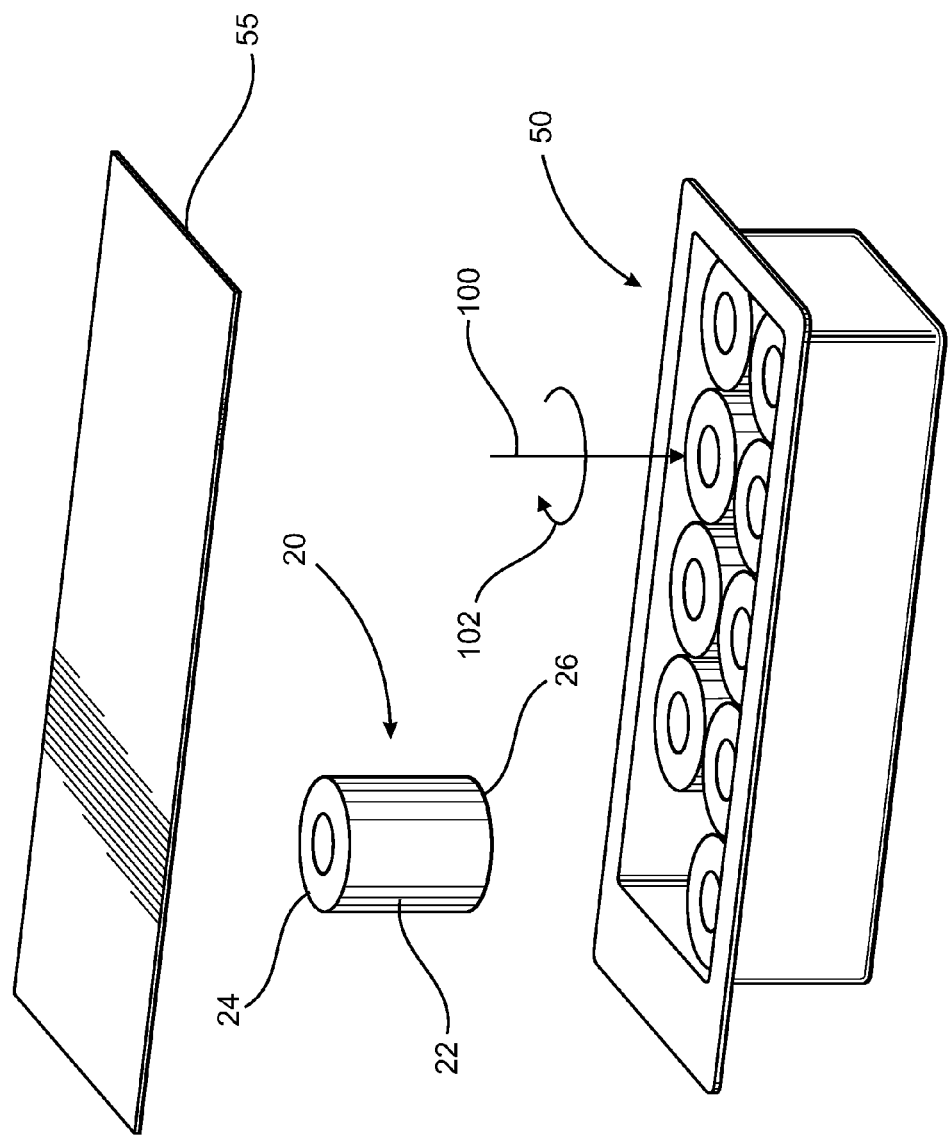
FIG. 1 is an exploded view of the closure and a support base for the closure, representing the present invention in at least one preferred embodiment.

In addition, the present invention as represented in the embodiments of FIGS. 1 and 3-14 comprises the closure 20, operatively associated with a support base 50 for one or more closures 20. With additional reference to FIGS. 11 through 14, the support base 50 may be a container 54 or alternatively integrated in to and considered a part of a container 54 having inner portions including, but not limited to, a base or floor 52 of the container 54. As such, the support base 50 can be accurately described as a floor portion, base portion or other inner portion 52 of the container 54, as is clearly depicted in FIGS. 11 and 12. As also disclosed, the container 54 may be structured to contain only one closure 20, but in preferred embodiments at least one closure 20, or a plurality of the closures 20, on the interior thereof as illustrated in FIGS. 1 and 11-13. Further, the container 54 may include a cover structure 55, as shown in FIG. 1, that is preferably, but not necessarily, formed of Tyvek® material produced by the E.I. DuPont Company, of Wilmington, Del. (or one or more of its subsidiaries).

Moreover, the container 54 may be structured to retain one or more of the closures 20 in an operative orientation. When so oriented, the closures 20 may be stored, shipped and made readily available in the "operative orientation," which facilitates the receipt of and attachment to a syringe 11, in the manner described hereinafter, once the cover 55 has been removed. In at least one embodiment of the present invention, once the cover structure 55 has been removed from the container 54, the "operative orientation" of a closure 20 may be more specifically described as comprising the closed end 28 of the closure 20 being disposed in removable mating engagement with a connector 56, while said open end 24 of the closure 20 is exposed to the syringe 11, in a manner which facilitates the rotational attachment between the syringe 11 and the closure 20. Accordingly, the operative orientation of the one or more closures 20, such as end cap members 22, when disposed on the one or more connectors 56 of the support base 50, facilitates the aligned insertion, as at 100 in FIG. 1, of a portion of the syringe 11 into the closure 20, and the aforementioned rotation of the syringe 11 relative to the closure or end cap 22. It is also emphasized that at least one preferred embodiment comprises the container 54 associated with the support base 50, and further, that at least one connector 56 is of the type structured to accomplish the "commercial packaging" of the one or more closure(s) 20, wherein such commercial packaging is intended for storage, transport, and delivery of the closure(s) 20 from a manufacturer or distributer to a point or location of use.

With further regard to the aforesaid cover structure 55 for the container 54, as shown in FIG. 1, it is noted that one advantage of forming the cover structure 55 and/or other portions of the container 54 from the aforementioned Tyvek® material is that it permits some passage of gas but resists the passage of liquid or moisture therethrough. As such, a sterilant gas can pass through the cover 55 of the container 54 and facilitate the desired sterilization of one or more closures 20. The sterilized condition of the one or more of the closures 20 can also be substantially or at least partially maintained both prior to and during their rotational attachment to a syringe 11, by eliminating or reducing the need to physically handle the closures 20 in order to accomplish the connection of the syringe 11 and the closure(s). As such, the attachment of the syringe 11 to or with any one of a plurality of closures 20 can be accomplished without a physical touching of the closures 20, by first disposing the nozzle portion 2' of the syringe in substantial axial alignment with the closure and leading portion 31 of the syringe cap 30, as schematically represented by directional arrow 100 in FIG. 1. Once so aligned, and further, when the interior threaded surface 3" of the syringe nozzle 2 is disposed in interacting, confronting relation with outwardly extending ears, tabs or at least partially threaded members 33 of the leading portion 31 of the syringe cap 30, the aforementioned "rotational attachment" can be accomplished by a rotation of the syringe 11 in a predetermined direction, such as is schematically represented by directional arrow 102 of FIG. 1, relative to the interconnected closure 20 between end cap member 22 and syringe cap 30, which at least initially is a fixed interconnection.

Figure 11:
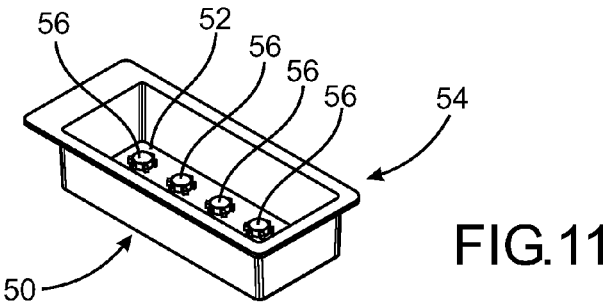
FIG. 11 is an interior, perspective view of the support base for one or more closures, also illustrated in the embodiment of FIG. 1, wherein the support base is in the form of a container.
Figure 12:
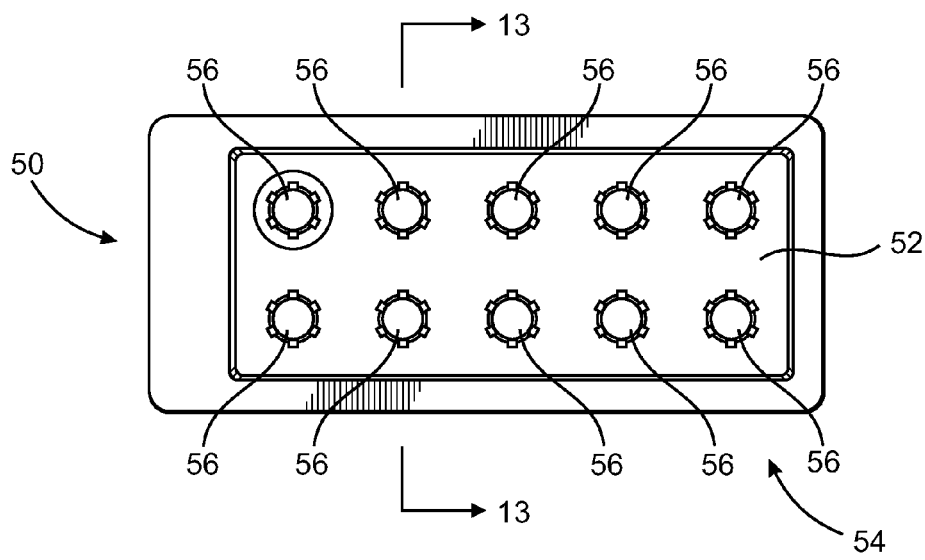
FIG. 12 is an interior, top plan view of the support base shown in the embodiment of FIGS. 1 and 11.
Figure 13:
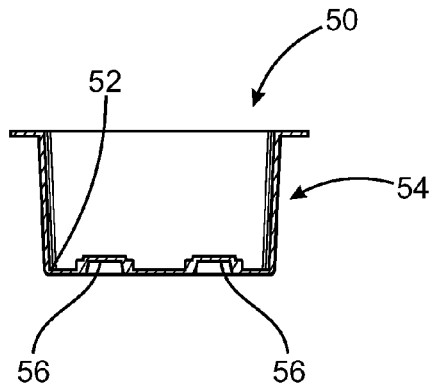
FIG. 13 is a transverse sectional view of the support base taken along line 13-13 of FIG. 12.

Moreover, the aforementioned "rotational attachment" is further facilitated by maintaining each of the closures 20 in a rotationally fixed position, while the closures 20 are in the upright operative orientation. More specifically, and due to the fact that the one or more closures 20 are removable from, but at least temporarily fixed within the interior of the container 54, in engaging relation with the support base 50 or container floor 52, the syringe 11 will be able to rotate, as at 102 in FIG. 1, relative to the substantially rotationally fixed position of the closure 20, thereby accomplishing the aforementioned rotational attachment between the syringe 11 and the closure 20. Referring now to FIGS. 11 and 12, in order to facilitate the support and operative orientation of the one or more closures 20 within the container 54, or more in particular, on the support base 50 or inner portion 52 thereof, a connecting structure comprising at least one or a plurality of connectors 56 are provided. The connecting structure in the form of one or more connectors 56 are integrally or fixedly connected to the support base 50 or inner portion 52 of the container 54. Moreover, each of the one or more connectors 56 is structured to interact with the exterior surface or outer portion of the closed end 28 of the closure 20 or end cap member 22. As is perhaps best illustrated in FIGS. 3 and 8, the closed end 28 includes a recess 60 formed on and extending within the exterior surface of the closed end 28 of the closure 20.

Still referring to FIGS. 9-13, the outwardly projecting one or more connectors 56 of the connecting structure are cooperatively disposed, dimensioned and configured to establish a removably mating engagement with the closed end 28 of the closure 20, preferably by being disposed and inserted within the recess 60 formed on or within the exterior surface of the closed end 28 of the end cap member 22. This cooperative structuring at least partially defines a "rotationally restrictive" connection between the closure 20 and more specifically, the closed end 28 and a corresponding one of the connectors 56. This cooperative structuring and "rotationally restrictive" engagement between the connector 56 and a correspondingly disposed recess 60 within the closed end 28 of the exterior of the end cap member 22 also serves to maintain the operative orientation of the corresponding closure 20 during transport of the support base 50 or container 54.

Accordingly, the "rotationally restrictive" connection may be more specifically defined with reference to FIGS. 9 and 10, as well as FIG. 21 hereinafter described. In more specific terms, the rotationally restrictive connection comprises the closure 20 being disposed in substantially rotationally fixed position relative to the one connector 56 and the support base 50, concurrently to a rotation of the syringe 11 relative to the closure 20, thereby facilitating the rotational attachment of the syringe 11 to the closure 20.

Figure 14:
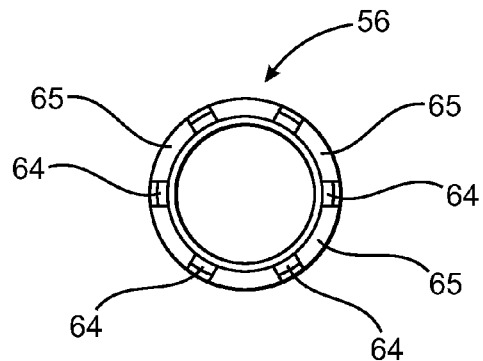
FIG. 14 is an exterior view of one of a possible plurality of connectors secured to and protruding outwardly from an interior of the floor of the support base and container of the embodiment shown in FIGS. 1 and 11 through 13.

As shown in FIGS. 8, 9 and 10, the closed ends 28 of the closures 20 and more specifically, of the end cap members 22 include a plurality of projections 62 formed at least partially on the interior side wall or interior peripheral surfaces of the corresponding recess 60. The plurality of projections 62 may vary in number and placement, but are cooperatively disposed, structured and dimensioned to interact with a second plurality of projections 64, shown in FIG. 14, formed on an outer surface or outer peripheral surface 56' of each of the connectors 56. Additional structural features include, as shown in FIGS. 9 and 10, the closed ends 28 having a plurality of open portions or spaces 63 formed between adjacent ones of the plurality of projections 62. Similarly, and as shown in FIG. 14, each of the one or more connectors 56 will preferably include open areas or spaces 65 between adjacent ones of the second plurality of projections 64. Therefore, the cooperative dimensions of the connectors 56 with or relative to the recesses 60 allow for an at least partial insertion of the connectors 56 into the interior of a correspondingly disposed one of the recesses 60 on closed end 28 of a closure 20. When this nesting or insertion occurs, the corresponding plurality of projections 62 of the closed end 28 of a closure 20, and the plurality of projections 64 on the connectors 56, will interact so as to be disposed in at least partially abutting, confronting, interrupting and/or blocking relation to one another.

For purposes of clarity, the projections 64 disposed on each of the one or more connectors 56, such as are illustrated in FIG. 14, will be referred to herein as a "first" plurality of projections, while the cooperatively disposed and structured projections 62 on the closed end 28 and/or within the recess 60 of the end cap member 22 shown in FIG. 9 will be referred to as a "second" plurality of projections. Moreover, this "first" and "second" terminology will be used in the description of the additional embodiments of the present invention, herein provided. Similarly, for purposes of clarity, the term "substantially rotationally fixed" is intended to describe, but not be limited to, the closure 20 being restricted from rotating relative to the one connector 56, to the extent that at least a minimal amount of rotational sliding or "slippage" type movement may occur there between. This would be due to the configurations and/or dimensions of confronting portions and/or surfaces, specifically including the interactions of the first plurality of projections 64 and the second plurality of projections of the connector 56 and the closed end 28 of closure 20, respectively, when disposed in the removable mating engagement with one another.

Accordingly, the closed end 28 of the closure 20 will be removably connected in a rotationally restrictive manner relative to a corresponding connector 56 on support base 50, such as the inner portion 52 of a container 54, by being substantially prevented from rotating relative to the connector 56 in either of two opposite directions. Moreover, the preferably fixed attachment of the closed end 28 to the closure 20 or end cap member 22 will thereby restrict the closure 20 from rotating relative to the inner portion 52 and connector 56 of the container 54 in either of two opposite directions. Therefore, each of the closures 20, once disposed in a container 54, in the aforementioned rotationally restrictive connection with corresponding ones of the connectors 56 on the inner portion 52 of the container 54, will be substantially restricted from rotating in either of two opposite directions. In addition, the aforesaid restrictive rotation of these structures which serves to fix or at least substantially rotationally fix the position of the closure 20 relative to the inner portion 52 of the container 54, will further serve to facilitate the alignment 100 shown in FIG. 1, of a syringe 11 with the interior of the syringe cap 30. This fixed positioning of the closures 20 in an operative orientation for receiving the syringe 11 therein also serves to facilitate the rotation 102 of the syringe 11 relative to the closure 20.

Accordingly, axial alignment of a syringe 11 as is meant to be illustrated by arrow 100 in FIG. 1, within a closure 20, and the rotation of the syringe 11 in the preferred, predetermined direction 102 shown in FIG. 1, once inserted into the syringe cap 30 of a closure 20, will result in an interactive engagement of the drive portions 42 and 44, shown in FIGS. 3, 7 and 8, and thereby, cause a fixed positioning of the syringe cap 30 relative to the end cap member 22 and support base 50, or more specifically, the connector 56 on the inner portion 52 of support base 50 and/or of a container 54. As a result, the aforementioned rotational attachment between the nozzle 2 of the syringe 11 and the syringe cap 30 will be made. Once such rotational attachment has been accomplished, an outwardly directed force or pulling force exerted on the syringe 11 will serve to remove the connected closure 20 from the interior of the container 54 and from its, operative orientation on the interior portion 52 of the support base 50. The attachment between the end cap member 22 of the closure 20 and the syringe 11 may thereby be accomplished without the need for the individual to touch or handle the closure 20 and/or end cap 22, which in turn, helps to maintain the sterility of the syringe and prevent contamination.

Importantly, the assembly of the present invention is versatile enough to be used in a different manner, such as without the support base 50 or container 54 including for one or more connector structures 56. More in particular, the closure 20 of the present invention can be manually removed from its engagement with an interior portion 52 of a container 54 and yet, still facilitate a permitted rotational attachment of the closure 20 to a syringe 11. Once so removed from a container 54, the corresponding closure 20 can be manually rotated relative to the syringe 11, and the aforementioned drive portions 42 and 44 of the drive assembly 40 will interact to facilitate the rotational attachment of the closure 20 and end cap member 22 to the syringe 11.

Figure 18:
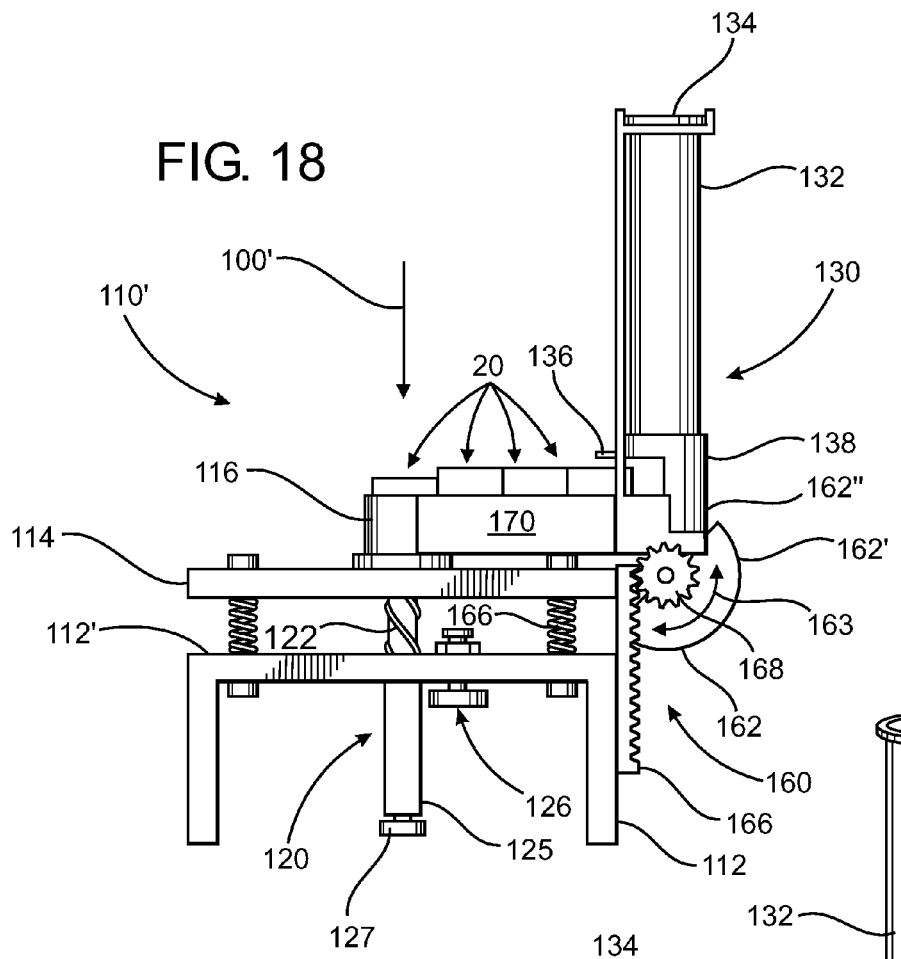
FIG. 18 is a side view of the present invention in yet another preferred embodiment and also relating to the substantially automatic attachment of one or a plurality of closure assemblies, each individually to a syringe, and which is operatively similar but structurally distinguishable from the embodiment shown in FIGS. 15 and 16.

Accordingly, and referring now to the embodiments illustrated in FIGS. 15-20, the present invention will be seen to include additional preferred embodiments directed to a substantially "automatic" attachment of one or more closures 20, such as the closure represented in FIG. 3, to one or more syringes 11. As used herein, the term "automatic" is meant to include, when referring to the embodiments of FIGS. 15-32, the ability to connect or interconnect a closure 20 and a syringe 11, without requiring a person to handle or touch the closure 20, while it is being rotationally attached to the syringe 11. As set forth in greater detail hereinafter, this inventive "automatic" or substantially "automatic" attachment or connection is accomplished by disposing and/or maintaining the closure 20 in another preferred operative orientation, such as is illustrated in FIGS. 15 and 16, and by concurrently rotating the closure 20 by virtue of the operational and structural features of a connecting assembly 110 and/or 110', as represented in FIGS. 15 and 18, respectively.

More specifically, and with initial reference now to FIGS. 15-17, an assembly is illustrated for securing a closure 20 to a syringe 11 in a substantially automatic manner. It is pointed out that the assembly is intended for use with a closure or cap for a syringe such as, but not limited to, the closure 20 having at least some of the same or at least similar structural features as have been described in detail herein with reference to FIGS. 1 and 3-14. Accordingly, the embodiment of FIGS. 15 and 16 comprises a connecting assembly 110 that includes a base 112, which may vary in structure and size, dependent upon the specific environment in which it is used. A platform 114 is movably connected to the base 112 and includes a connecting structure in the form of a closure receiving structure or cup 116. As clearly represented in FIG. 17, the connecting structure in the form of closure receiving cup 116 includes at least one connector, generally indicated as 118. The connector 118 has similar structural and operative features as connectors 56, which have been described previously herein with reference to FIGS. 1 and 3-14. However, and as should be apparent, the at least one connector 118 of FIG. 17 is fixedly secured to and preferably disposed within the connecting structure which here, is closure receiving cup 116. Moreover, the connector 118 illustrated in this embodiment is cooperatively structured to interact with the recess 60 in the closed end 28 of the closure 20 so as to establish the previously mentioned "rotationally restrictive" connection therebetween. As such, a closure 20, having an end cap member 22 with a closed end 28, is disposed in removable mating engagement with the one connector 118, and serves to establish a rotationally restrictive connection with the closure 20 and maintains it in an operative orientation. This preferred operative orientation is demonstrated in FIGS. 1, 15-16, as well as in FIGS. 18 and 19, and facilitates the receiving of a syringe 11 and its rotational attachment to the corresponding closure 20.

Referring again to FIGS. 15-17, the connecting structure 116 of the assembly 110, as well as the one connector 118, is rotationally mounted on the platform 114. Moreover, the connecting structure in the form of closure receiving cup 116, as well as the one connector 118, move with the platform 114 between a receiving position and a connecting position. The receiving position is represented in FIGS. 15 and 16, and is at least partially defined by the closed end 28 of the end cap member 22 and closure 20, being disposed in the removable, mating engagement with the one connector 118. At the same time, the closure 20 is disposed in the aforementioned operative orientation, wherein the open end thereof is exposed to the syringe 11 so as to facilitate receiving of the syringe 11, as represented in FIG. 16. The platform 114 is also capable of being disposed in the connecting position, wherein the platform 114 and the connecting structure cup 116 move closer to the upper or corresponding end 112' of the base 112.

More specifically, the aforesaid, connecting position is at least partially defined by the syringe 11 being disposed within the end cap member 22 and being at least partially rotationally connected to the closure 20 and/or syringe cap 30. It is emphasized that when the platform 114 of connecting assembly 110 moves into the connecting position, it is forced downwardly towards the corresponding upper end 112' of the base 112. Moreover, the downward movement of the platform 114 occurs concurrently to the rotation of the connecting structure 116 and the connector 118. Accordingly, and with reference to FIG. 15, the inventive assembly includes a drive linkage, which in the illustrated embodiment comprises a rotary drive linkage assembly 120 mounted on or otherwise directly associated with the connecting assembly 110. The rotary drive linkage assembly 120 preferably includes at least a first member which is preferably, but not necessarily, in the form of an elongated screw gear 122, and a second member disposed on the interior of the base 112 in driving and/or mating engagement with the first member or elongated screw gear 122. Therefore, a forced downward movement of the platform 114 towards and relative to the upper end 112' of the base 112 will result in a concurrent rotation of the connecting structure or cup 116 and the one connector 118, due to the interaction of the elongated screw gear 122 and the drive member associated with the base portion 112'. Further, the linearly or axially directed force, represented by arrow 100' in FIG. 16, causing the downward movement of the platform 114, connecting structure 116, connector 118 and closure 20, from the receiving position of FIG. 15 into the connecting position of FIG. 16, is caused by the syringe 11 engaging the closure 20 in substantially axial alignment therewith.

In the preferred embodiments of the invention, the connecting assembly 110 will also include a biasing assembly, such as but not limited to one or more biasing elements or springs 124. As a result, the one or more biasing elements or springs 124 are disposed and structured to normally bias the support platform 114 and the connecting structure 116 away from the top of the base 112' and into the receiving position, as represented in FIG. 15. Accordingly, a predetermined downward force 100', which is schematically represented in FIG. 16, exerted by the syringe 11, will be transferred to the closure 20 and connecting structure in the form of closure receiving cup 116. This will result in the platform 114 moving away from and out of the receiving position of FIG. 15, and towards the base portion 112' and into the aforementioned connecting position. Upon a release of the downwardly directed force 100', the biasing force exerted on the platform 114 by the one or more biasing springs 124, will cause the platform 114 to automatically return to the receiving position shown in FIG. 15.

The upward travel of the platform 114 may also result in a rotation of the connecting structure or cup 116, one connector 118 and the closure 20 in an opposite direction. However, due to the structure and operation of the drive assembly 40, as described in detail above, the syringe cap 30 and the syringe 11 rotationally attached thereto, will not rotate in the opposite direction with the end cap 22, and the syringe 11 will not become disconnected from the closure 20.

Still referring to FIGS. 15-17, this embodiment will preferably include at least one adjustment assembly, generally indicated as 126. The adjustment assembly 126 may assume a variety of structures and is disposed to determine or limit the amount of downward travel of the platform 114 relative to the base portion 112'. This, in turn, will limit the amount of rotation of the connecting structure 116 and of the at least one connector 118, and the rotation of the end cap member 22 and closure 20 being secured to the syringe 11. Therefore, at least one purpose of the adjustment assembly 126 is to accommodate different structural and dimensional characteristics of any of a plurality of different syringes 11. More specifically, the threaded interconnection between the outwardly extending ears, tabs or threaded portions 33 of the syringe cap 30 (best shown in FIG. 3) and the interior threads 3" of the syringe 11, (best shown n FIG. 2) may require a different amount of rotation and/or threaded engagement between the syringe cap 30 and the threaded portion 3" dependent upon the size of the syringe 11 (whether a small 1-cc syringe, 10-cc syringe, 50-cc syringe or larger) and/or outer diameter of the syringe 11. The adjustment assembly 126 is structured to limit not only the distance to and/or position into which the platform 114 travels into the connecting position towards the base portion 112,' but also the amount of rotation of the connecting structure or cup 116 and closure 20 contained therein.

In additional preferred embodiments, the present invention is directed to an "automatic" assembly and/or system for securing each of a plurality of closures 20 to a different one of a plurality of syringes 11. More specifically, and with reference to FIGS. 18-22, the connecting assembly 110' includes a base 112, an upper base portion 112', a platform 114, a connecting structure or cup 116, a rotary drive linkage assembly 120, and at least one adjustment assembly 126. In addition, the connecting structure 116 includes the at least one connector 118 connected thereto and movable therewith, as between the receiving position of the platform 114 as represented in FIGS. 15 and 18, and the connecting position, as described above.

Figures 19, 20:
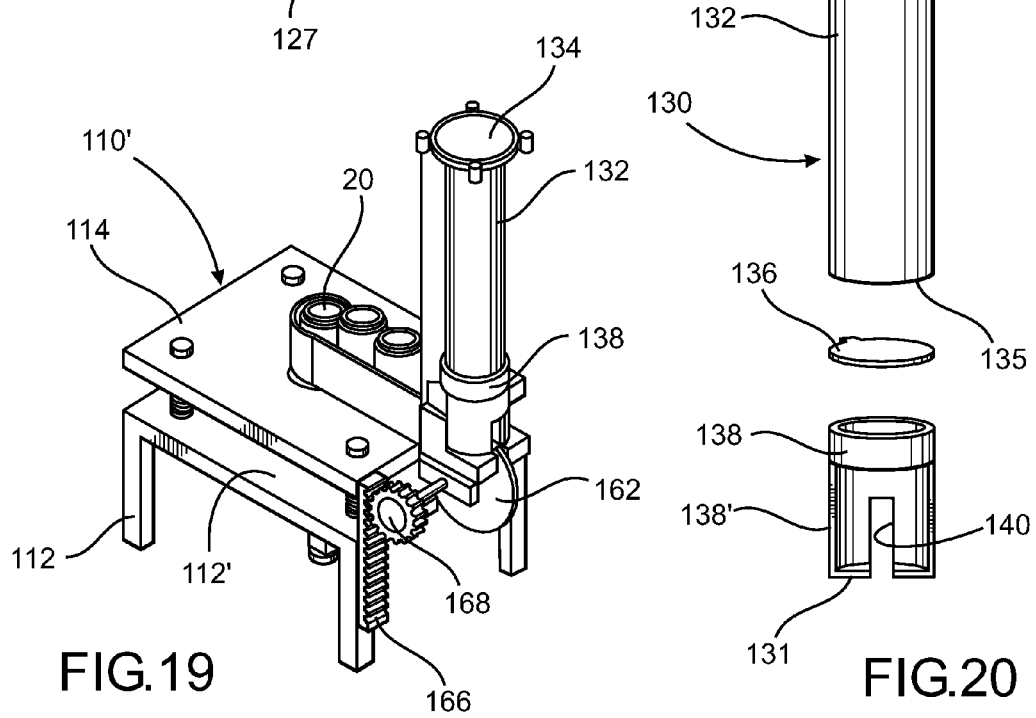
FIG. 19 is a perspective view of the invention shown in the embodiment of FIG. 18.
FIG. 20 is a perspective view in exploded form of a canister associated with the invention shown in the embodiment of FIGS. 18 and 19.

However, and as shown in FIGS. 18-19, structural variations of the connecting structure 110' include a biasing assembly comprising at least one biasing spring 124 mounted within the interior of a sleeve or like structure 125. The enclosed spring is disposed and structured to exert a biasing force on the first member or screw gear 122 tending to force the platform 114 upwardly into the receiving position, as also described above. It is of further note that the biasing force exerted by the one or more biasing springs 124 may be adjusted through at least a second adjustment assembly 127 connected to the sleeve or like structure 125.

Yet another embodiment of the present invention comprises an automatic assembly and system as represented in FIGS. 18-22, including a supply assembly, generally indicated as 130 and a positioning assembly, generally indicated as 160. More specifically, the supply assembly 130, includes a closure supply in the form of a canister or like container 132 dimensioned and configured to contain a plurality of the closures 20 therein. Further, and as shown in FIG. 20, the canister or container 132 includes a closed end 134 and an oppositely disposed open end 135. The open end 135 is disposed and dimensioned to allow for a closure 20 to exit, or a plurality of closures 20 to exit successively there through, once a seal or closure structure 136 has been removed. The seal structure 136 is preferably formed from a Tyvek™ material. As set forth above, the advantages of utilizing the Tyvek™ material is that this material is gas permeable, but resistant to the passage of liquid or moisture. Therefore, a sterilizing gas can pass through the seal 136 so as to facilitate the closures 20, contained within the interior of the canister 132, being maintained in a sterilized condition. In use, closure supply or the canister 132 of the supply assembly 130 is arranged in what may generally be referred to as an inverted position or orientation, as represented in FIGS. 18-19.

When so positioned, and as shown in FIG. 18, the open end 135 directly communicates with the positioning assembly 160, and more specifically, with an adapter 138. The adapter 138 is operatively disposed in interconnecting relation between the canister 132 and the positioning assembly 160, such as being connected directly adjacent to the open end 135. The adaptor 138 also includes a stop member 139, as shown in FIG. 20, which facilitates the stopping or retaining of each of the closures 20 as they exit from the canister 132 through the open end 135. Accordingly each closure 20, once it has exited from the interior of the canister 132, will pass substantially into the interior 138' of the adapter 138, as shown in FIG. 20. When so positioned, the closure 20 will be retained by the stop member 139 and thereby, be prevented from falling out of or away from the connecting structure 110' and/or the positioning assembly 160.

As represented in FIG. 20, the adapter 138 also includes at least one opening or passage 140 disposed and structured to cooperate with the operation of the positioning assembly 160. Specific structural and operative features of the positioning assembly 160 include a positioning member 162 connected in cooperative "positioning engagement" with individual ones of the closures 20 as they exit from the interior of the canister 132 through the open end 135. As schematically represented by directional arrow 163 in FIG. 18, the positioning member 162 is reciprocally movable by virtue of its fixed connection to a connecting shaft or rod 164, shown in FIG. 19. In turn, the positioning assembly 160 includes a driving member 166 and a driven member 168. In at least one preferred embodiment, the driving member 166 and the driven member 168 collectively define a rack and pinion gear assembly. However, other driving assemblies may be utilized to force the positioning member 162 into the aforementioned rotationally reciprocal movement 163 and into the aforementioned positioning engagement successively with each of a plurality of closures 20 as they exit from the canister 132.

Therefore, upon a downward force as indicated by directional arrow 100' in FIG. 18 being delivered to the syringe 11, as shown in FIGS. 16 and 18, the platform 114 will move from the receiving position of FIGS. 15 and 18 into the aforementioned and described connecting position. This downward movement will cause a corresponding movement or travel of the driving member 166 and a concurrent rotation of the driven member 168. In turn, the positioning member 162 will be forced to rotate towards a closure 20 disposed on the interior 138' of the adapter 138 and into the positioning engagement therewith through the opening 140 in the adapter 138. This will force the engaged closure 20 along a channel 170 defining a path of travel, shown in FIG. 19. As such, the first closure 20 in the aligned plurality of closures 20, disposed in a generally stacked array within the canister 132, will successively pass into the interior of the connecting structure 116 and into mating engagement with the one connector 118. The corresponding closure 20 engaging the connector 118 will be maintained in the aforementioned operative orientation so as to facilitate receipt of a syringe 11 therein, as illustrated in FIG. 16. A next "interior" closure 20, disposed immediately adjacent the open end 135, will be poised to pass therethrough and fall, under the influence of gravity, into the interior 138' of the adapter 138.

Moreover, the elongated configuration of the canister 132 of the supply assembly 130 will serve to axially align a plurality of closures 20 therein. Once each of the closures 20 exit through the open end 135, they will be oriented such that the closed end 28 of each of the closures 20 will be disposed to assume the removable, mating engagement with one connector 118 within the connecting structure 116. The opposite or open end 24 of each of the end cap members 22 and/or closures 20 will be positioned in an outwardly or upwardly exposed relation to the corresponding syringe 11, to facilitate the rotational attachment between the syringe nozzle portion 2 and the syringe cap 30.

In another embodiment, the present invention comprises yet another system and assembly structured to automatically secure at least one closure 20 and preferably, a plurality of such closures to different ones of a plurality of syringes 11, so as to cover or seal the discharge port 4. While at least operationally similar to the embodiments of FIGS. 15 through 20, the additional preferred embodiment of an automatic securing assembly is represented in FIGS. 23 through 32. As will become apparent from this description, substantially common features associated with the "automatic" embodiments of FIGS. 15-17 and 23-32 include the provision of a connecting assembly 210 including at least one connector 218 structurally and operatively connected to or considered a part of a connecting structure 216, which may be in the form of a receiving cup, similar to the connecting structure cup 116 represented as part of the embodiment of FIGS. 18 and 19. As disclosed in FIGS. 21 and 28, the one connector 218 is disposed on the interior of the connecting structure cup 216 and is dimensioned and configured to substantially correspond to and facilitate a removable mating engagement with the closed end 28 of each of the plurality of closures 20.

Figure 21:
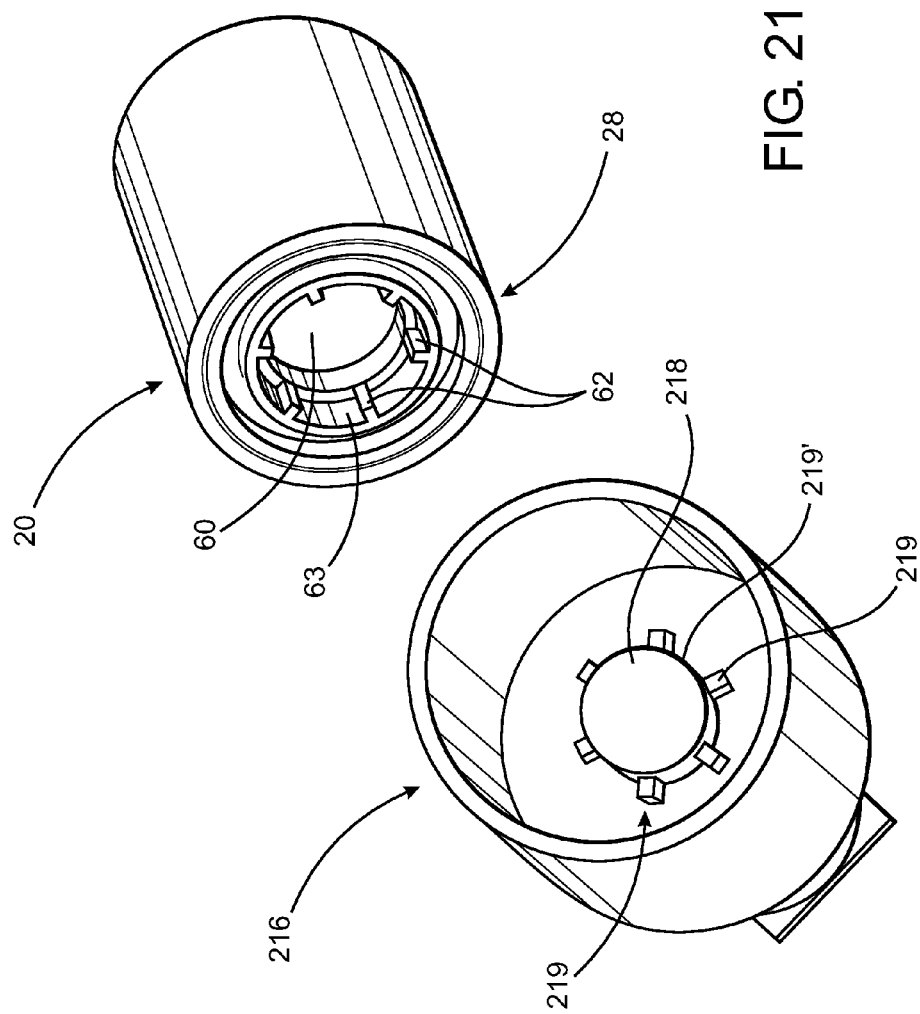
FIG. 21 is a perspective view in exploded form including corresponding structural features of a connector structure and a corresponding closure.

Accordingly, and as illustrated in FIG. 21, the one connector 218 is structurally and operationally similar to the connectors 56 and 118 and comprises a first plurality of outwardly extending projections 219, which may be disposed in an annular array and substantially equally or appropriately spaced from one another by spaces 219' about an outer and/or outer peripheral surface 219" of the connector 218. As such, the configuration of the one connector 218 will substantially correspond to the configuration and structure of the closed end 28 of the closure 20. Therefore, and as has been previously described and depicted in FIGS. 9 through 14, the closed end 28 of the closure 20 includes the recess 60 and a second plurality of projections 62 formed therein. The second plurality of recesses 62 are arranged in a corresponding, substantially annular or circular array and are equally or other wise appropriately spaced from one another by consecutive spaces 63, as is shown in FIGS. 8 and 9. Therefore, the one connector 218 is correspondingly configured to establish a removable mating engagement with the predetermined portion, including the recess 60, and the closed end 28 of the closure 20.

It is further emphasized that the configuring of the one connector 218 to correspond to the closed end 28 is not a mere design feature. To the contrary, this correspondingly configured structuring of the connector 218 with the closed end 28 facilitates a substantially automatic, error free "drop-in" positioning of each of the closures 20 onto the connector 218, in each of the preferred embodiments of the present invention. While other structural configurations have been attempted, the structuring of the one connector 218 with the closed end 28 of the closure 20 substantially eliminates or significantly reduces the occurrence of misalignment when automatically or manually positioning each of the closures in the operative orientation on a corresponding connector, so as to establish the rotationally restrictive engagement between a connector such as 218, and the closed end 28 of a corresponding closure 20.

Figure 22:
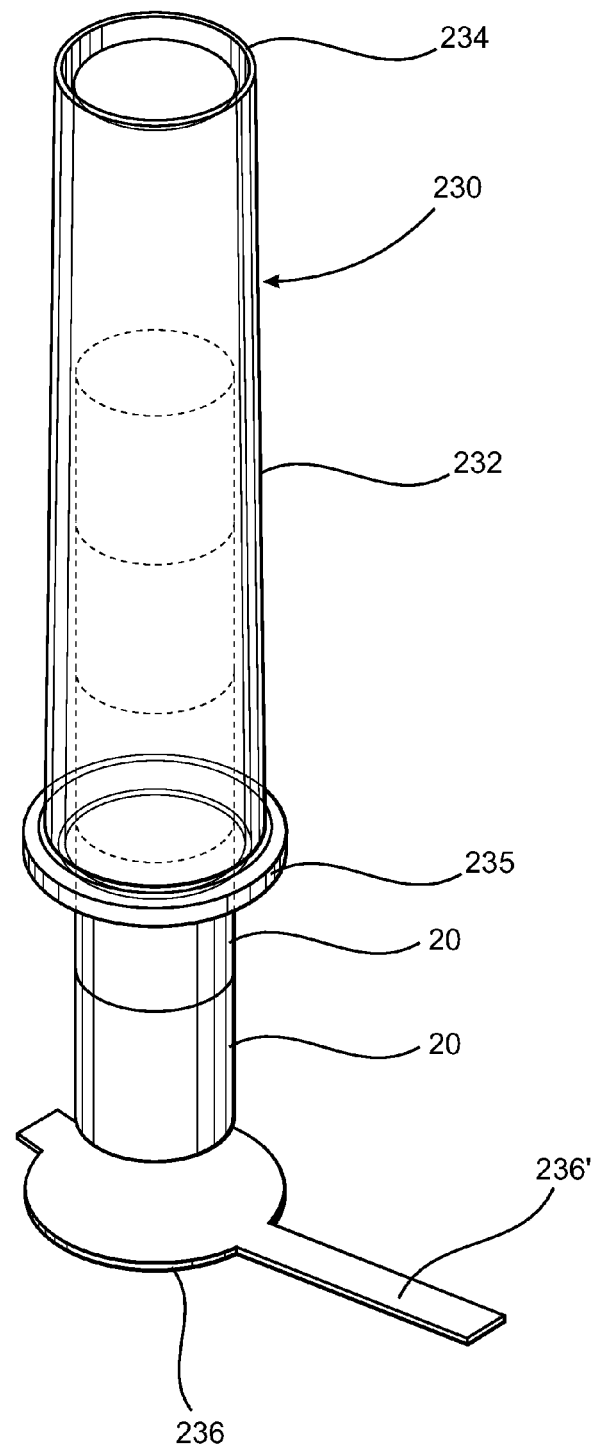
FIG. 22 is a perspective view of a supply assembly in the form of a cartridge.

Referring now to FIGS. 23-32, and also similar to the embodiments of FIGS. 15 through 17, at least one application of the additional automatic securing assembly may include the provision of a closure supply 230 in the form of a canister or magazine 232, as is best represented in FIG. 22. As such, the dimension and configuration of the canister 232 facilitates a substantially stacked or inline orientation of a plurality of closures 20 on the interior of the canister 232. In such an array, the closures will successively exit from the open end 235 preferably, but not exclusively, by gravitational feed. Also, a seal 236 may be in the form of a Tyvek® lid which may be removable from the open end 235 by exerting a pulling or other appropriate force on the outwardly extending tab 236'.

Figure 27:
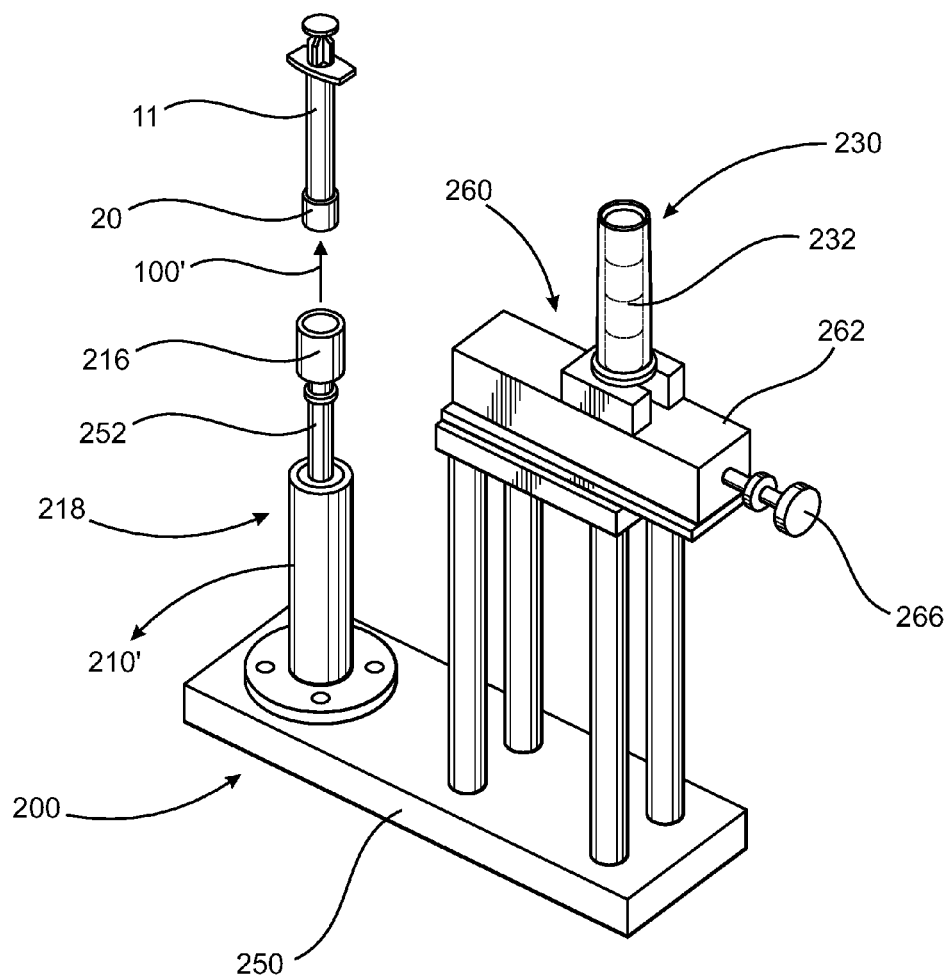
FIG. 27 is a perspective view of the embodiments of FIGS. 23 through 26 of the next succeeding step of operation.
Figure 28:
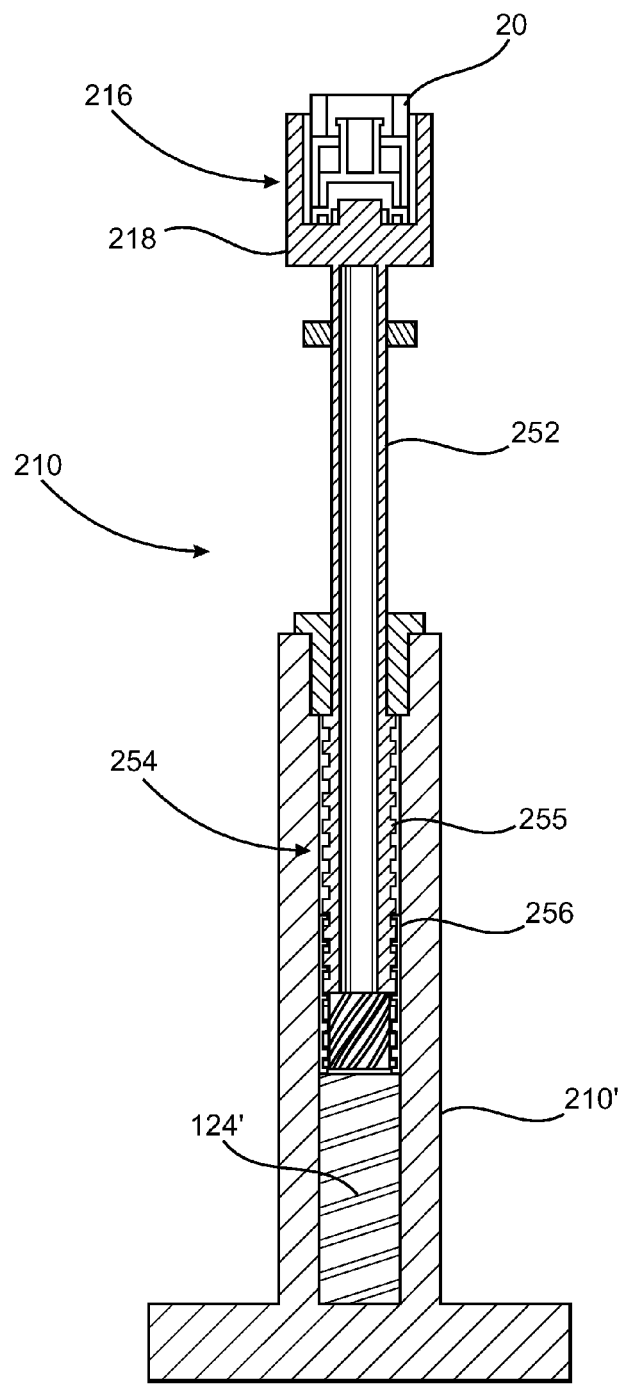
FIG. 28 is a longitudinal sectional view showing interior operative portions of a connecting structure associated with the invention illustrated in the embodiments of FIGS. 23 through 27.

With primary reference to FIGS. 23 through 28, the additional preferred embodiment of the automatic closure securing assembly is generally represented as 200. More specifically, a connecting assembly 210 includes an elongated configuration and is preferably mounted on a base or other supporting surface 250, and further, includes an outer casing or housing portion 210'. Structural and operative features of the connecting assembly 210 are represented in FIG. 28 and include the receiving or connecting structure or cup 216 having at least one connector 218 mounted on the interior thereof. Further, the connecting structure cup 216 is connected to an outer or distal end of an elongated shaft as at 252, shown in FIGS. 25 and 28. A rotary linkage assembly is generally indicated as 254 and includes interacting gears 255 connected to the shaft 252 and rotational therewith. A cooperating gear structure is indicated as 256 and may be secured to or mounted on interior portions of the casing or housing 210'. Accordingly, the gear structures 255 and 256 of the gear assembly 254 collectively define the rotary linkage assembly, which may be in the form of a screw gear. As such, the linkage assembly is disposed and structured to force rotation of the one connector 218 and connecting structure 216, as well as the closure 20 disposed in an operative orientation thereon, relative to the casing 210'. More specifically, the drive linkage comprising the gear assembly 254 is disposed and structured to translate applied force 100 into linear movement of the one connector and concurrent rotational movement of the one connector 218. Such linear movement will be exerted on the closure 20 and connector 218 by a downward or other appropriate directional force on the syringe 11, co-axial to the gear 252, when it engages the corresponding closure 20 disposed in the operative orientation, as represented in FIG. 23. As represented in FIG. 28 a return spring 124' will be disposed within the 210' and serves to return the gear 252 into the receiving position from the connecting position as described above with reference to FIGS. 15 and 16.

Additional features of the securing assembly and system of FIGS. 23 through 32 include the provision of a carriage assembly 260 disposable between a delivering position, as represented in FIG. 25 and a closure supplied position, as represented in FIG. 23. As such, the carriage assembly 260 includes the carriage 262 movably mounted on a supporting track assembly 265 connected to and supported by the aforementioned base 250. In addition, a positioning assembly 264 is connected to the carriage and movable therewith and is preferably, but not exclusively, in the form of a plunger or other exteriorly accessible member 266. Disposition and structure of the positioning assembly 264 including the at least one positioning member 266 is schematically represented in FIGS. 29 through 32, and will be discussed in greater detail hereinafter. In addition, intended or selected manipulation of the positioning member 266 will cause the movement of the carriage 262 between the closure supplied position of FIG. 23 and the closure delivering position as represented in FIG. 26. Concurrently, the structural and operative features of the positioning assembly 264, specifically including the positioning member or plunger 266 will concurrently and successively contact each of the closures 20 by a "positioning engagement" therewith, as schematically represented in FIGS. 29 through 32.

Figure 29:
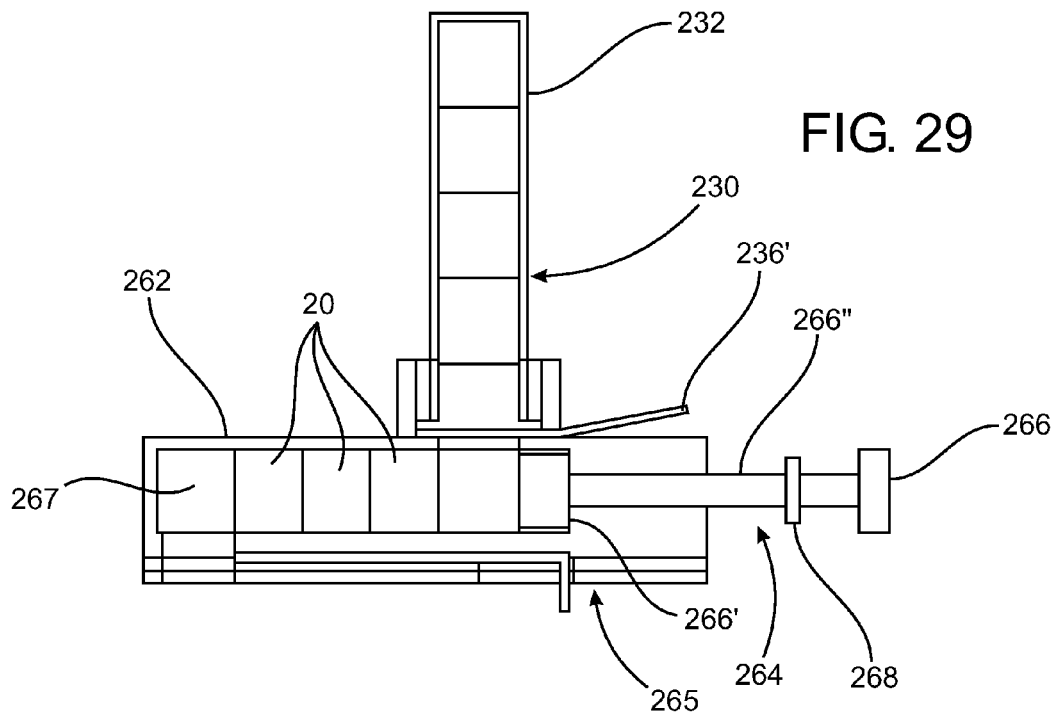
FIG. 29 is a schematic representation of FIGS. 23-27 in one stage of operation.
Figure 31:
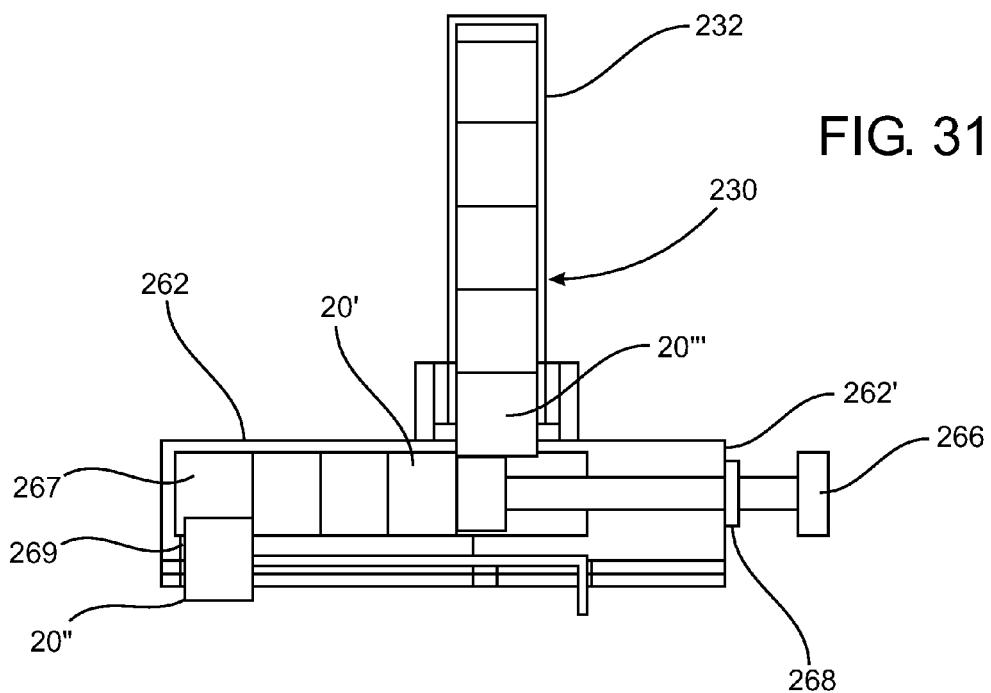
FIG. 31 is a schematic representation of FIGS. 23-27 in yet another stage of operation.
Figure 30:
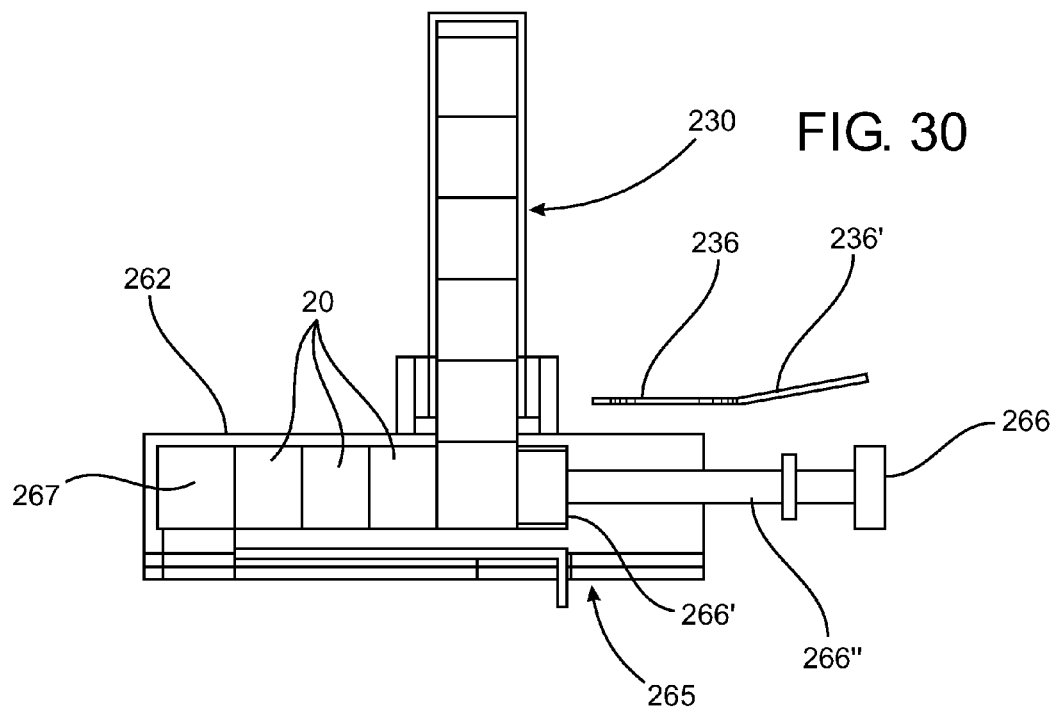
FIG. 30 is a schematic representation of FIGS. 23-27 in a different stage of operation.

The structural and operational features of the automatic securing assembly 200 are also represented in FIGS. 29 through 32, as set forth above. More specifically, FIG. 29 is substantially equivalent to the assembly 200 as represented in FIG. 23. As such, a plurality of closures 20 are mounted on or within the carriage 262 and are sequentially delivered or "indexed" into a delivering portion 267 of the carriage 262, when the carriage 262 is disposed into the closure delivering position of FIG. 26. Therefore, in FIGS. 29 and 30 closures 20 substantially fill the appropriate location on or within the carriage 262, thereby allowing the positioning member 266 to be manipulated by extending inwardly until the stop or retaining member 268 engages a corresponding portion 262' of the carriage 262, as represented in FIG. 31. Inward movement of the positioning member 266 will cause the head portion 266' to engage the inner most closure 20', forcing the outer-most closure 20" into the delivering portion 267 of the carriage 262 and into a delivering orientation relative to the connecting structure 216 and connecting member 218. Once so positioned, the delivering portion 267 is appropriately structured to allow the outer most closure 20" to assume the delivering orientation, wherein it will fall or pass through passage 269 or otherwise be removed from the carriage 262 into the connecting structure cup 216 and into the mating engagement with the connector 218.

The delivering portion 267 may be at least partially defined by an end location on or within the carriage 262 which will be aligned with a passage 269. Such alignment with the passage 269 will allow the closure 20" to fall there through into the interior of the connecting structure cup 216 and into the aforementioned mating engagement with the connector 218. As indicated, the corresponding configuration of the connector 218 and the recess 60 of the closed end 28 of the closure 20 facilitate an automatic and substantially error-free, mating engagement between the closed end 28/recess 60 and the one connector 218. Upon passage of the end most closure 20' into the connecting structure cup 216, the positioning member 266 will be retracted as demonstrated in FIG. 32. Such outward movement of the plunger or positioning member 266 will cause the carriage 262 to move from the delivering position back into the closure supplied position of FIGS. 26 and 32. It is of further note that the head portion 266' of the plunger or positioning member 266 is disposed, configured and dimensioned to retain the next closure 20''', which is about to fall from the canister 232, from completely exiting through the open end 235, until the positioning member 266 and the head 266' is completely retracted into the position represented in FIG. 32. Once the head 266' is so retracted, gravity feed will facilitate the passage of the closure 20''' from the interior of the canister 232 into the carriage 262, as demonstrated by a comparison of the structures of FIGS. 31 and 32.

The retainer or stop member 268 mounted on the shaft 266" of the positioning member 266 is specifically disposed relative to the head 266' so as to accomplish successive "indexing" of the plurality of closures mounted on the carriage 262. As a result, continued reciprocal, inward and outward movement of the positioning member 266, will cause successive disposition or indexing of the closures 20 into the delivering portion 267 and into the delivering orientation as represented in FIG. 31.

The additional preferred embodiment of FIGS. 23 through 32 are represented in use with a closure supply 230, including canister 232. However, it is possible that the carriage 262 could be modified, along with the positioning member 266, to be operative to dispose a single closure into the delivery portion 267. In the operation thereof, the single closure 20 could be disposed into the delivery portion 267 and eventually through the passage 269. The modification of the carriage 262 and/or the positioning member 266 could include, but not be limited to, an adjustment of the overall length of the positioning member 266 or the position of the retainer or stop member 268.

Figure 32:
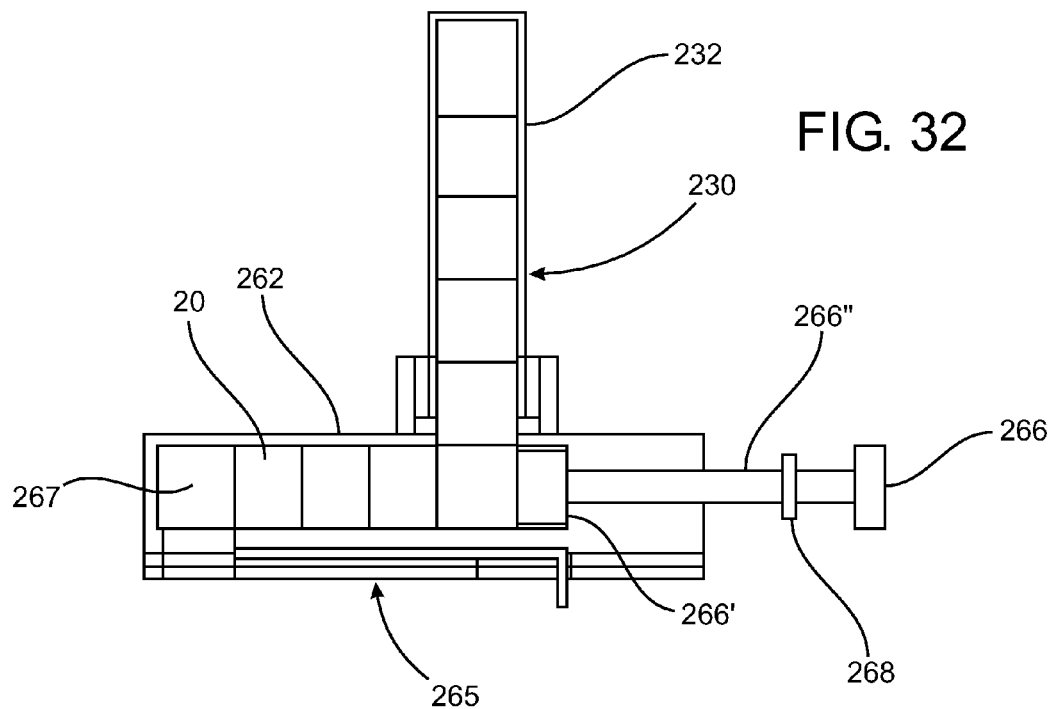
FIG. 32 is a schematic representation of FIGS. 23-27 in yet another stage of operation.

Finally, FIG. 27 represents the carriage 262 in its completely retracted position as also represented in FIG. 32. When so retracted, the movement of the connecting assembly 210 and/or connecting member 218 between the aforementioned receiving position and connected position will cause the corresponding closure 20 to be rotationally attached to the syringe 11 in closing or sealing relation to the discharge port 4 thereof. Thereafter, the removal of the syringe 11 and the closure 20 attached thereto is indicated by the directional arrow 100'. In turn, this will remove of reduce the linearly applied force 100 on the positioning assembly 220, as represented in FIG. 23, allowing the connector to return to the receiving position. Such automatic return may be due in part to the provision of a biasing assembly or spring(s) as explained in greater detail with regard to the embodiment of FIGS. 15, 20, 23 and/or 28. Due to the operative and structural features of the above described rotary drive 254, movement of the connecting assembly 210 from the connecting position to the receiving position, the cause the connecting structure 216 and the connector 218 to rotate in an opposite direction from that when the connecting structure cup 216 rotates when the connecting assembly 210 passes from the receiving position into the connecting position. However, due to the structure of a drive assembly 40 (see FIG. 3), the closure 20, once connected to the syringe 11 as represented in FIG. 27, will not rotate relative to the syringe 11 or become detached there from.

Figure 33:
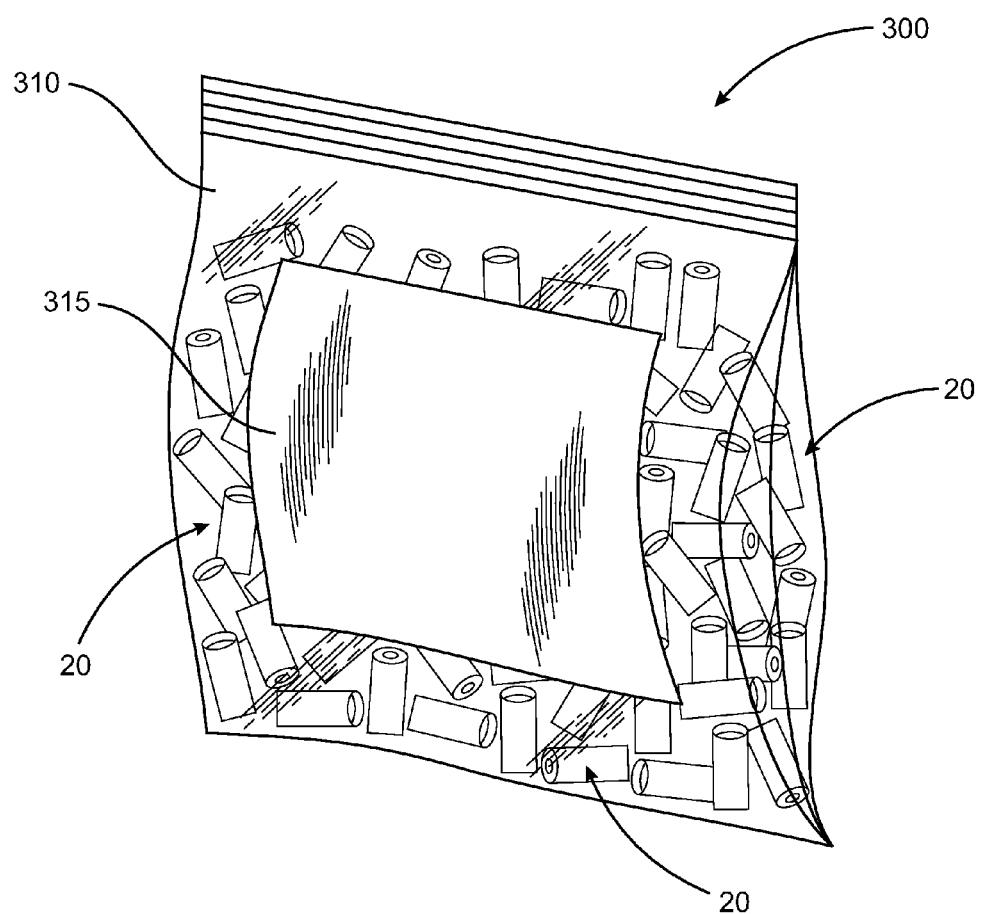
FIG. 33 is a perspective view of one embodiment of a closure supply of the present invention.

Turning now to FIG. 33, at least one embodiment of the assembly for closing a discharge port of a syringe includes a closure supply 300 made up of a container 310 and a plurality of closures 20 retained therein. As with other containers or supplies disclosed above, the closure supply 300 shown in FIG. 33 stores multiple closures 20 for delivery, sterilization, and storage until use. More specifically, the container 310 is sufficiently sized to accommodate many closures 20 therein, which are disposed in a random arrangement within the container 310. That is to say, there is no particular order or arrangement of the closures 20 held within the container 310, and they are not fixed in a particular location or relation to one another. Moreover, the container 310 may be any size to accommodate any predetermined number of closures 20. By way of example only, one size container 310 may be used to retain a maximum of twenty-five closures 20; a larger sized container 310 may hold a maximum of one hundred closures 20. Accordingly, different sizes may be used depending on capacity, need, or other relevant factors.

As is evident from FIG. 33, the container 310 is made of a non-rigid, at least somewhat flexible material which may assume any of a number of shapes. For example, the container 310 may be a bag or other similar structure capable of retaining materials therein and taking on various shapes as dictated by the contents. Such container 310 may be transparent, such as for viewing of the contents therethrough, or may be opaque such that the contents are not visible, or any degree of visibility therebetween.

Moreover, the container 310 is structured to facilitate the exposure of the various closures 20 contained therein to a sterilizing fluid. Specifically, the container 310 includes certain structure which facilitates the passage of a sterilizing fluid through at least a portion of the container 310. For example, the container 310 may include at least one section of gas permeable material 315, such as Tyvek® material produced by the E.I. DuPont Company, of Wilmington, Del. (or one or more of its subsidiaries). As previously discussed, Tyvek® material permits some passage of gas but resists the passage of liquid or moisture or microbes there through. As such, a sterilant gas can pass through the section of gas permeable material 315 of the container 310 and facilitate the sterilization of one or more closures 20 held therein. The sterilized condition of the one or more of the closures 20 is substantially or at least partially maintained as long as the container 310 remains sealed or closed.

Accordingly, once the container 310 is filled with closures 20, such as at a manufacturing site, the container 310 is sealed or closed. The filled container 310 is then subjected to a sterilant gas, which penetrates through the gas permeable material 315 of the container 310 until the closures 20 are fully sterilized. Since the container 310 is closed, the interior space and closures 20 residing therein are maintained in a sterile environment. Once sterilized, the container 310 may be shipped for delivery and/or stored for a time. Of course, sterilization may occur at any location, such as after delivery, and in some cases the container 310 may be subjected to multiple rounds of sterilization, if needed.

Upon use, the container 310 may be unsealed or temporarily opened to facilitate the removal of a closure(s) 20 as needed. It should be appreciated that such unsealing or opening may be performed manually, such as by a person working in a sterile environment such as under a "hood," or mechanically, such as by a machine, which may be an automated or programmed process. The closures 20 are removably retained within the container 310, so that each closure 20 may be individually removed from the container 310 when needed. It is contemplated that, to maintain the sterility of the interior chamber of the container 310 and the remaining closures 20 held therein, that the container 310 is only opened so far and for only as long as is needed to remove the desired closure 20 at the time it is needed, and is resealed or closed as soon as possible following the removal of the needed closure(s) 20. As can be appreciated, this process may be repeated any number of times as is needed to remove closure(s) 20 as they are needed.

It should also be apparent from FIG. 33 that the container 310 lacks any connecting structure as discussed above, such as connectors 56 or cups 116. Accordingly, the container 310 of the closure supply 300 is not directly connected to any part of the closures 20. The closures 20, therefore, are randomly disposed within the container 310 and may move freely about therein, and are free to rotate within the container 310, subject to the limitations of the boundaries of the container 310 itself and the space available between adjacent closures 20 in close proximity within the closure supply 300.

Now that the invention has been described,
What is claimed is:

1. An assembly for closing a discharge port of a syringe, said assembly comprising:
    at least one closure including a closed end and an open end, said one closure structured for rotational attachment to the syringe,
    a connecting structure including at least one connector mounted on said connecting structure and movable therewith, said one connector cooperatively structured with said one closure to define a rotationally restrictive connection there between,
    said rotationally restrictive connection comprising a substantially rotationally fixed positioning of said closed end and said one connector concurrent to rotation of said one closure and said one connector relative to the syringe,
    drive linkage connected to said connecting structure and operative to move said connecting structure and said one closure between a receiving position and a connecting position,
    said drive linkage disposed and structured to translate linear movement of said one closure and said one connector between said receiving and connecting positions to concurrent rotation of said one connector and said one closure relative to the syringe, and
    said drive linkage structured to rotate said one closure into said rotational attachment with the syringe, concurrent to disposition of said connecting structure and said one closure from said receiving position to said connecting position, upon a predetermined, substantially linear directed force applied, by the syringe, to said one closure, substantially co-axially to said drive linkage.

2. An assembly as recited in claim 1 wherein said drive linkage comprises an elongated screw gear.

3. An assembly as recited in claim 1 wherein said one connector is correspondingly configured to said closed end to define said substantially rotationally fixed positioning and a removable mating engagement there between.

4. An assembly as recited in claim 3 wherein said closed end comprises a recess formed on an exterior thereof and extending inwardly into said closed end; said one connector disposed in outwardly protruding relation from said connecting structure, said one connector disposed within said recess to establish said removable mating engagement with said closed end.

5. An assembly as recited in claim 4 further comprising an outer surface formed on said one connector and an inner surface formed within said recess; said outer surface and said inner surface being cooperatively dimensioned and configured with one another to at least partially define said rotationally restrictive connection of said one closure and said one connector when said one connector and said closed end are in said removable mating engagement with one another.

6. An assembly as recited in claim 5 wherein said one connector comprises a first plurality of projections formed on said outer surface thereof; said recess comprising a second plurality of projections formed on said inner surface thereof; said first and second plurality of projections relatively disposed and cooperatively structured to at least partially define said rotationally restrictive connection, when said one connector and said recess are in said removable mating engagement with one another.

7. An assembly as recited in claim 6 wherein said first and second plurality of projections are cooperatively disposed and structured for interruptive, movement restricting engagement with one another; said movement restricting engagement at least partially defining said rotationally restrictive connection to include a restrictive rotation of said closure in either of two opposite directions relative to said one connector.

8. An assembly as recited in claim 1 wherein said receiving position comprises said one closure disposed in an operative orientation on said connecting structure; said operative orientation comprising said closed end disposed in said removable mating engagement with said one connector and said one open end exposed to the syringe in a position facilitating said rotational attachment to the syringe.

9. An assembly as recited in claim 8 wherein said connecting position comprises said connecting structure being displaced from said receiving position and the syringe being at least partially disposed in said rotational attachment to said one closure.

10. An assembly for closing a discharge port of a syringe, said assembly comprising:
    at least one closure including an open end and a closed end; said one closure structured for rotational attachment to the syringe,
    said connecting structure including at least one connector mounted thereon and movable therewith, said one connector structured for removable mating engagement with said closed end of said one closure,
    said one connector correspondingly configured and cooperatively structured with said closed end to define a rotationally restrictive connection between said one connector and said one closure,
    said rotationally restrictive connection comprising a substantially rotationally fixed positioning of said one closure on said one connector in an operative orientation and a concurrent rotation of said one closure with said one connector relative to the syringe,
    a delivery assembly structured for support and positioning of said one closure into a delivering orientation relative to said connecting structure and said one connector; said delivering orientation comprising said one closure disposed in aligned relation with said operative orientation, and
    a platform connected to said connecting structure and movable therewith between a receiving position and a connecting position; said connecting structure and said one connector rotationally disposed on said platform and movable therewith between said receiving and connecting positions.

11. An assembly as recited in claim 10 wherein said delivery assembly comprises a carriage assembly structured for movable support of said one closure and selective disposition into and out of a delivering position relative to said one connector; a positioning assembly comprising at least one positioning member disposable in positioning engagement with said one closure and structured for positioning thereof into said delivering orientation relative to said one connector; said positioning member movable with and relative to said carriage; said positioning member disposed and structured in driving relation to said carriage and concurrent positioning of said one closure into said delivery orientation.

12. An assembly as recited in claim 11 wherein said carriage includes a delivering portion disposable in direct communicating relation with said one connector when said carriage is in said delivering position; said delivering portion and said positioning member being cooperatively structured to dispose said one closure into said delivering orientation.

13. An assembly as recited in claim 11 wherein said carriage is structured for concurrent support of a plurality of said closures; said positioning member structured for successive positioning engagement with each of said plurality of closures and an indexing thereof into said delivering orientation relative to said one connector.

14. An assembly as recited in claim 13 further comprising a closure supply disposed in communicating relation with said carriage; said closure supply comprising a canister structured to contain a plurality of closures and disposed in communicating relation with said carriage.

15. An assembly as recited in claim 10 further comprising a closure supply including a plurality of closures disposable in communicating relation to said delivery assembly, said delivery assembly including a positioning member operatively structured to dispose individual ones of a plurality of closures into said operative orientation; said positioning member configured to be disposed in positioning engagement with a last exiting one of a plurality of closures from said closure supply and in concurrently retaining engagement with a next adjacent one of a plurality of closures within the closure supply.

16. An assembly as recited in claim 15 wherein said closure supply comprises a canister dimensioned and configured to maintain a plurality of closures in successively aligned relation to one another, said canister disposable in communicating relation to said delivery assembly, said communicating relation of said canister at least partially defined by a gravitational feed of said plurality of closures from said canister to said positioning member.

17. An assembly as recited in claim 16 further comprising an adapter disposed in interconnecting relation between said canister and said positioning member; said adapter structured to position individual ones of said plurality of closures from said canister to said positioning assembly.

18. An assembly as recited in claim 15 wherein said positioning member is structured for positioning engagement of each of said plurality of closures and successive disposition thereof into said operative orientation relative to said one connector.

19. An assembly as recited in claim 10 wherein said connecting position is variably disposed relative to said receiving position, said variable disposition at least partially dependent on dimensional characteristics of the syringe.

20. An assembly as recited in claim 10 comprising at least one adjustment assembly attached to said connecting structure and selectively disposable to determine each of a plurality of variable locations of said connecting position relative to said receiving position.

21. An assembly as recited in claim 10 further comprising a closure supply including a container having a plurality of randomly disposed closures removably retained therein; said container structured to facilitate exposure of said retained closures to a sterilizing fluid by passage thereof through at least a portion of said container.

22. An assembly as recited in claim 21 wherein said container comprises at least one section of gas permeable material formed thereon.

23. An assembly as recited in claim 22 wherein said gas permeable material comprises Tyvek.

\* \* \* \* \*